(12) United States Patent
Ota et al.

(10) Patent No.: US 8,110,662 B2
(45) Date of Patent: Feb. 7, 2012

(54) ANTIBODY DIRECTED TO PROTEIN INVOLVED IN MAINTAINING DIFFERENTIATION OF SMOOTH MUSCLE CELLS

(75) Inventors: Toshio Ota, Tokyo (JP); Takao Isogai, Ibaraki (JP); Tetsuo Nishikawa, Tokyo (JP); Koji Hayashi, Osaka (JP); Kaoru Otsuka, Saitama (JP); Jun-Ichi Yamamoto, Chiba (JP); Shizuko Ishii, Chiba (JP); Tomoyasu Sugiyama, Tokyo (JP); Ai Wakamatsu, Chiba (JP); Keiichi Nagai, Tokyo (JP); Tetsuji Otsuki, Chiba (JP); Shin-Ichi Funahashi, Ibaraki (JP); Shoji Miyata, Kanagawa (JP); Kenji Sobue, Osaka (JP); Kenichiro Hayashi, Osaka (JP)

(73) Assignees: Chugai Seiyaku Kabushiki Kaisha, Tokyo (JP); Kenji Sobue, Osaka (JP)

(*) Notice: Subject to any disclaimer, the term of this patent is extended or adjusted under 35 U.S.C. 154(b) by 0 days.

(21) Appl. No.: 11/869,267

(22) Filed: Oct. 9, 2007

(65) Prior Publication Data
US 2008/0069826 A1 Mar. 20, 2008

Related U.S. Application Data

(60) Division of application No. 11/051,410, filed on Feb. 4, 2005, now Pat. No. 7,279,558, which is a division of application No. 10/058,518, filed on Jan. 28, 2002, now Pat. No. 6,908,748, which is a continuation-in-part of application No. PCT/JP00/005059, filed on Jul. 28, 2000.

(60) Provisional application No. 60/159,590, filed on Oct. 18, 1999, provisional application No. 60/183,322, filed on Feb. 17, 2000.

(30) Foreign Application Priority Data

Jul. 29, 1999 (JP) ..................................... 11-248036
Jan. 11, 2000 (JP) ................................. 2000-118776
May 2, 2000 (JP) ................................. 2000-183767

(51) Int. Cl.
*C07K 16/00* (2006.01)
*A61K 39/00* (2006.01)

(52) U.S. Cl. ............... 530/387.9; 530/387.1; 424/184.1; 424/185.1

(58) Field of Classification Search ........................ None
See application file for complete search history.

(56) References Cited

U.S. PATENT DOCUMENTS 7,060,811 B2 * 6/2006 Aldaz et al. ................. 536/23.5

OTHER PUBLICATIONS

Attwood Science 290: 471-473, 2000.*
Skolnick et al. Trends in Biotech. 18: 34-39, 2000.*
Lederman et al. Molecular Immunology 28: 1171-1181, 1991.*
Li et al. PNAS 77: 3211-3214, 1980.*
Houghten et al. New Approaches to Immunization, Vaccines 86, Cold Spring Harbor Laboratory, p. 21-25, 1986.*
Bost et al. Immunological Investigation, 1988, 17:577-586.*
Bendayan J. Histochem. Cytochem. 1995; 43:881-886.*
Aoki, et al. (1999). Inhibition of the p53 tumor suppressor gene results in growth of human aortic vascular smooth muscle cells. Potential role of p53 in regulation of vascular smooth muscle cell growth. Hypertension. 34(2):192-200.
Bednarek, et al. (2000). WWOX, a novel WW domain-containing protein mapping to human chromosome 16q23.3-24.1, a region frequently affected in breast cancer. Cancer Res. 60(8):2140-2145.
Bednarek, et al. (2001). WWOX, the FRA16D gene, behaves as a suppressor of tumor growth. Cancer Res. 61(22):8068-8073.
Chang, et al. (2001). Hyaluronidase induction of a WW domain-containing oxidoreductase that enhances tumor necrosis factor cytotoxicity. J Biol Chem. 276(5):3361-3370.
Gmerek, et al. Database Genbank Accession No. U13395. National Library of Medicine, Bethesda, MD, Sep. 15, 1994.
International Preliminary Examination Report dated Dec. 10, 2001.
Maskos, et al. (1998). Crystal structure of the catalytic domain of human tumor necrosis factor-α-converting enzyme. Proc Natl Acad Sci USA. 95(7):3408-3412.
Nishida, et al. (1997). Analysis of gene expression control mechanism in smooth muscle cell transformation (differentiation and dedifferentiation). Cell Technology. 16(10):1496-1508.
Paige, et al. (2001). WWOX: a candidate tumor suppressor gene involved in multiple tumor types. Proc Natl Aced Sci USA. 98(20):11417-11422.
Yakicier , et al. (2001). Identification of homozygous deletions at chromosome 16q23 in aflatoxin B1 exposed hepatocellular carcinoma. Oncogene. 20(37):5232-5238.

* cited by examiner

*Primary Examiner* — Sharon Wen
(74) *Attorney, Agent, or Firm* — Fish & Richardson P.C.

(57) ABSTRACT

A cDNA fragment participating in the maintenance of smooth muscle differentiation was isolated using a culture system of chicken gizzard smooth muscle cells, the differential display method and the subtracted hybridization method. Using the obtained cDNA sequence as a query, cDNA sequences of Helix Research Institute (Japanese Patent Application No. 2000-118776) were retrieved, and thus, a novel gene "C-NT2RP3001495" was obtained. The protein encoded by this gene has two WW domains that participate in protein interactions in the N-terminal domain. Evidence suggests that this protein binds to other proteins, and thus regulates the intracellular signal transduction, gene expression, and so on, thereby participating in the maintenance of the differentiation of smooth muscle cells. This protein and compounds regulating the expression thereof are markedly useful in developing drugs for various diseases associated with abnormality in the maintenance of smooth muscle cell differentiation.

2 Claims, 1 Drawing Sheet

ANTIBODY DIRECTED TO PROTEIN INVOLVED IN MAINTAINING DIFFERENTIATION OF SMOOTH MUSCLE CELLS

This application is a divisional of U.S. application Ser. No. 11/051,410, now U.S. Pat. No. 7,279,558, filed Feb. 4, 2005 now U.S. Pat. No. 7,279,558, which is a divisional of U.S. application Ser. No. 10/058,518, now U.S. Pat. 6,908,748, filed Jan. 28, 2002, which is a continuation-in-part of PCT/JP00/05059, filed Jul. 28, 2000, which claims priority to U.S. Provisional Application Nos. 60/159,590, filed Oct. 18, 1999, and 60/183,322, filed Feb. 17, 2000; and Japanese Patent Application Nos. 11-248036, filed Jul. 29, 1999; 2000-118776, filed Jan. 11, 2001; and 2000-183767, filed May 2, 2000.

TECHNICAL FIELD

The present invention relates to novel human proteins associated with the maintenance of differentiation of smooth muscle cells.

BACKGROUND

The smooth muscle cell is a major muscle cell in tissues such as blood vessel, trachea, digestive tract, urinary bladder, and uterus, and its important function is the regulation of contraction and relaxation. Recently, a relationship has been revealed between phenotypic modulation of the smooth muscle cells, wherein the cell looses the contraction ability and thereby acquires proliferation ability, and the pathological state. The proliferation of vascular smooth muscle cell is closely associated with the manifestation of the pathological state such as restenosis occurring after percutaneous transluminal coronary angioplasty (PTCA). It has been clarified that vascular tunica media smooth muscle cells acquire motility through phenotypic modulation to a dedifferentiated type in the early stage of the onset of arteriosclerosis, and thus, migrate to the vascular endothelium, which is the major cause of hypertrophy of vascular endothelium. However, there are still many obscure points about the phenotypic modulation of smooth muscle cells, for example, associated genes, molecular mechanism thereof, and so on. A better understanding of how the smooth muscle cells maintain the differentiated phenotype and how their phenotypes are converted to the dedifferentiated type is needed to develop therapeutic methods for morbid states caused by smooth muscle cell proliferation. The mechanism of the phenotypic modulation may be elucidated by analyzing the genes associated with the maintenance of differentiated type of smooth muscle cells, such genes being applicable as therapeutic agents and diagnostic agents for diseases caused by the aberrant proliferation of smooth muscle cells; ischemic heart diseases such as arteriosclerosis, myocardial infarction, aortic aneurysm, and cerebral apoplexy; cerebral vascular disorders; and vascular dementia. In addition, glomerulonephritis, pulmonary fibrosis, cerebral arteriosclerosis, and hepatitis, which correspond to a state of aberrant proliferation of mesangial cells, alveolar epithelial cells, pericytes, and Ito cells, respectively—cells that have extremely similar characteristics to the smooth muscle cells—are presumed to be diseases caused by cellular transformation occurring through a mechanism similar to that of smooth muscle cells; and thus, the genes therein may also be applicable as therapeutic agent and diagnostic agent for these chronic diseases.

SUMMARY

The object of the present invention is to provide novel proteins associated in the maintenance of differentiation of smooth muscle cells, genes encoding them, and production and use of the proteins and genes.

To accomplish the objects described above, the present inventors vigorously carried out the following research. The present inventors first constructed a cDNA library by subtracting cDNAs of dedifferentiated smooth muscle cells derived from chicken gizzard from cDNAs of differentiated smooth muscle cells derived from-chicken gizzard, in order to elucidate the mechanism for the maintenance of differentiation of smooth muscle cells. The nucleotide sequence of the obtained cDNA fragment was determined, and thus a sequence (SEQ ID NO:3) named "12F08" was obtained. It has been revealed that "12F08" exhibits a homology of 82% to the clone Hs#S1388556 belonging to a human Unigene cluster Hs.128045.

In the next step, the present inventors obtained the "Hs128045_12F08con" sequence by preparing a contig via assembling sequences belonging to the human Unigene cluster Hs.128045. The pfam motif database was then searched for the "Hs128045_12F08con" by utilizing estwisedb in the database search program Wise2 designed by Ewan Birney at Sanger Center. The results showed that each of 12F08 and Hs128045_12F08con contained two WW domains that are important functional domains for protein-protein interaction.

Furthermore, the present inventors searched cDNA sequences of Helix Research Institute (helix clones; Japanese Patent Application No. Hei 11-248036; Japanese Patent Application No. 2000-118776) for homologues using the above-mentioned sequence, "Hs128045_12F08con", obtained from Unigene Cluster as a query. These helix clones are highly expected to have the full length sequence, which are obtained by the combined use of: [1] preparation of cDNA library, which comprises cDNA having a full-length sequence at a high rate, by the oligo-capping method; and [2] evaluation system for the cDNA to determine whether it contains the full-length sequence based on the 5' end sequence (the selection is achieved based on the evaluation using ATGpr after eliminating non-full length clones as compared with an EST). The results of homology search showed that the query clone was identical to the helix clone "C-T2RP3001495". In addition, it was also revealed that the query clone is identical to the gene for Hs.519 Human oxidoreductase (HHCMA56) of Unigene. However, the sequence of HHCMA56 contains reading mistakes of nucleotides, and thus it has been deposited as a gene encoding a protein consisting of 371 amino acids which is entirely different from the protein of "C-NT2RP3001495". Thus, it can be stated that "C-NT2RP3001495" is a novel protein found for the first time by the present inventors. The "C-NT2RP3001495" is a protein consisting of 414 amino acids, which has two WW domain sequences.

The present inventors then analyzed the expression level of gene "12F08" in a variety of tissues by real-time PCR. The results showed that the gene was expressed at high levels in the differentiated smooth muscle and gizzard, suggesting that "12F08" encodes a protein associated with the maintenance of differentiation of smooth muscle cells. Thus, human "C-NT2RP3001495" is presumed to be a protein associated with the maintenance of differentiation of smooth muscle cells.

The human "C-NT2RP3001495" is expected to be useful as a pharmaceutical for diseases caused by the aberrant proliferation of smooth muscle cells; ischemic heart diseases such as arteriosclerosis, myocardial infarction, aortic aneurysm, cerebral apoplexy; cerebral vascular disorders; and vascular dementia; as well as for glomerulonephritis, pulmonary fibrosis, cerebral arteriosclerosis, and hepatitis, which correspond to the states of aberrant proliferation of mesangial cells, alveolar epithelial cells, pericytes, and Ito cells, respectively—cells which have extremely similar characteristics to the smooth muscle cells.

As described above, the present inventors found novel proteins associated with the maintenance of differentiation of smooth muscle cells, and thereby accomplished the present invention.

Specifically, the present invention relates to novel proteins which participate in the maintenance of differentiation of smooth muscle cells, genes encoding the proteins, and production and uses of the proteins and genes. More specifically, the present invention provides the following:

[1] a DNA of any one of the following (a) to (d):

(a) a DNA encoding a protein consisting of the amino acid sequence of SEQ ID NO:2, (b) a DNA comprising the coding region of the nucleotide sequence of SEQ ID NO:1, (c) a DNA encoding a protein which (i) comprises the amino acid sequence of SEQ ID NO:2 in which one or more amino acids are substituted, deleted, inserted and/or added, and (ii) is functionally equivalent to the protein consisting of the amino acid sequence of SEQ ID NO:2, and (d) a DNA hybridizing under a stringent condition to a DNA consisting of the nucleotide sequence of SEQ ID NO:1, which encodes a protein functionally equivalent to the protein consisting of the amino acid sequence of SEQ ID NO:2;

[2] a DNA encoding a partial peptide of a protein consisting of the amino acid sequence of SEQ ID NO:2;

[3] a protein or peptide encoded by the DNA of [1] or [2];

[4] a vector into which the DNA of [1] or [2] has been inserted;

[5] a host cell containing the DNA of [1] or [2], or the vector of [4];

[6] a method for producing the protein or peptide of [3], which comprises the steps of culturing the host cell of [5], and recovering the expressed protein from the host cell or the culture supernatant;

[7] an antibody binding to the protein of [3];

[8] a polynucleotide containing at least 15 nucleotides complementary to a DNA consisting of the nucleotide sequence of SEQ ID NO:1 or the complementary strand thereof; and

[9] a method of screening for a compound that binds to the protein of [3], which comprises the steps of:

(a) contacting a test sample containing at least one compound with the protein or a partial peptide thereof, (b) detecting the binding activity of the compound with the protein or a partial peptide thereof, and (c) selecting the compound that has the activity of binding to the protein or a partial peptide thereof.

The present invention provides a human-derived gene "C-NT2RP3001495" that encodes a novel protein which participates in the maintenance of differentiation of smooth muscle cells. The nucleotide sequence of human-derived cDNA "C-NT2RP3001495" is shown in SEQ ID NO:1, and the amino acid sequence encoded by the cDNA is shown in SEQ ID NO:2. As seen in SEQ ID NO:1, the human cDNA "C-NT2RP3001495" has an ORF encoding a protein consisting of 414 amino acids.

The inventive human "C-NT2RP3001495" gene has been selected as a helix clone (Japanese Patent Application No. Hei 11-248036; Japanese Patent Application No. 2000-118776) exhibiting homology to the cDNA fragment "12F08", isolated as a gene fragment associated with the maintenance of smooth muscle differentiation by using culture system of chicken gizzard smooth muscle cells. High expression of the above-mentioned "12F08" was observed in differentiated smooth muscle and gizzard. Further, the results of a motif search showed that the protein contained two WW domains in the N-terminal region that participate in protein-protein interaction. This suggests that the protein binds to other proteins and regulates intracellular signal transduction, gene expression or the like, and thereby participates in the maintenance of differentiation of smooth muscle cells. Further, the human "C-NT2RP3001495" protein of the present invention has an Adh short motif that is found in oxidoreductases and dehydrases, and therefore, it is potentially an oxidoreductase or dehydrase itself.

The expression pattern and structural properties of human "C-NT2RP3001495" suggest that it serves an important function in living body, and thus, it can be a useful target for drug development. In addition, compounds binding to human "C-NT2RP3001495" and compounds regulating human "C-NT2RP3001495" gene expression are expected to be applicable for the development of prophylactic or therapeutic agents for a variety of diseases caused by abnormalities in the maintenance of differentiation of smooth muscle cells.

Further the present invention includes proteins functionally equivalent to the human "C-NT2RP3001495" protein (SEQ ID NO:2). Such proteins include, for example, mutants, homologues, and variants of the human "C-NT2RP3001495" protein. The term "functionally equivalent" herein means that the protein of interest has a function associated with the maintenance of differentiation of smooth muscle cells like that of the "C-NT2RP3001495" protein. Specifically, the smooth muscle cells can be divided into two types, namely differentiated and dedifferentiated types thereof, by utilizing the expression of genes, such as the expression of calponin gene or h-caldesmon gene, which are characteristic of regulations at the transcription level and at the mRNA splicing level that are known as characteristics of the differentiated state (Cell Technology, 16(10):1496 (1997)). The levels of gene expression are compared between the differentiated cells and dedifferentiated cells prepared from the smooth muscle cells in which genes characteristic of the differentiated type are expressed. When the expression level of a gene is significantly higher or alternatively lower in the differentiated smooth muscle cells than in dedifferentiated cells, then it can be determined that it is highly probable that the gene has a function associated with the maintenance of differentiation. For example, chicken gizzard smooth muscle cells are included in smooth muscle cells in which genes characteristic of the differentiated type are expressed.

One method for preparing functionally equivalent proteins well known to those skilled in the art involves the introduction of mutations into the proteins. For example, one skilled in the art can prepare proteins functionally equivalent to the human "C-NT2RP3001495" protein (SEQ ID NO:2) by introducing appropriate mutations into the amino acid sequence of the protein using the site-directed mutagenesis method (Hashimoto-Gotoh, et al., Gene 152:271-275, 1995; Zoller et al., Methods Enzymol. 100:468-500, 1983; Kramer, et al., Nucleic Acids Res. 12:9441-9456, 1984; Kramer et al., Methods. Enzymol. 154:350-367, 1987; Kunkel, Proc. Natl. Acad. Sci. USA. 82:488-492, 1985; Kunkel, Methods Enzymol. 85:2763-2766, 1988) and such. Mutation of amino acids may occur in nature, too. The proteins of the present invention include proteins comprising the amino acid sequence of human "C-NT2RP3001495" protein (SEQ ID NO:2) in which one or more amino acids are mutated, so long as the resulting mutant protein is functionally equivalent to the protein. In such a mutant protein, the number of the amino acids to be mutated is usually 50 residues or less, preferably 30 residues or less, and more preferably 10 residues or less (e.g., 5 residues or less).

The amino acid residue to be mutated is preferably mutated into a different amino acid that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes of amino acids).

It is well known that a protein having deletion, addition, and/or substitution of one or more amino acid residues in the sequence of a protein can retain the original biological activity (Mark et al., Proc. Natl. Acad. Sci. U.S.A. 81:5662-5666, 1984; Zoller et al., Nucleic Acids Res. 10:6487-6500, 1982; Wang et al., Science 224:1431-1433; Dalbadie-McFarland et al. Proc. Natl. Acad. Sci. U.S.A. 79:6409-6413, 1982).

A protein having the amino acid sequence of human "C-NT2RP3001495" protein to which one or more amino acid residues have been added, is exemplified by a fusion protein containing the human "C-NT2RP3001495" protein. Fusion proteins, in which the human "C-NT2RP3001495" protein is fused to other peptides or proteins, are included in the present invention. Fusion proteins can be made using techniques well known to those skilled in the art, for example, by linking the DNA encoding the human "C-NT2RP3001495" protein (SEQ ID NO:2) in frame with the DNA encoding other peptides or proteins, followed by inserting the DNA into an expression vector and expressing it in a host. There is no restriction as to the peptides or proteins to be fused to the protein of the present invention.

For instance, known peptides which may be used for the fusion include the FLAG peptide (Hopp et al., BioTechnology 6:1204-1210, 1988), 6× His that is made up of six histidine residues, 10× His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, and Protein C fragment. Also, glutathione-S-transferase (GST), influenza hemagglutinin (HA), the constant region of immunoglobulin, β-galactosidase, maltose binding protein (MBP), and the like may be used as a protein to be fused with the protein of this invention. Fusion proteins can be prepared by fusing the DNA encoding these peptides or proteins, which are commercially available, with the DNA encoding the protein of the invention, and expressing the fused DNA.

An alternative method for preparing functionally equivalent-proteins known to those skilled in the art utilizes, for example, the hybridization technique (Sanbrook et al., Molecular Cloning 2nd ed. 9.47-9.58, Cold Spring Harbor Lab. Press, 1989). Generally, one skilled in the art can isolate DNAs highly homologous to the whole or part of the DNA sequence encoding the human "C-NT2RP3001495" protein (SEQ ID NO:1), and then isolate proteins functionally equivalent to the human "C-NT2RP3001495" protein based on those DNAs isolated. The present invention includes proteins that are (i) encoded by a DNA hybridizing to a DNA encoding the protein of human "C-NT2RP3001495" and (ii) functionally equivalent to the human protein of "C-NT2RP3001495". Such proteins include, for example, homologues derived from human and other animals (for example, protein encoded by a DNA from mouse, rat, rabbit, cattle, chicken, etc.). The protein (SEQ ID NO:4) encoded by "12F08" may be exemplified as the homologue from chicken.

Those skilled in the art can properly select hybridization conditions to be used for the isolation of DNAs encoding proteins functionally equivalent to the human protein of "C-NT2RP3001495". Hybridization conditions include low stringent conditions. Low stringent conditions may be, for example, 42° C. in 2×SSC and 0.1% SDS, preferably 50° C. in 2×SSC and 0.1% SDS for washing after hybridization. More preferably, high stringent conditions such as 65° C. in 0.1×SSC and 0.1% SDS may be chosen. DNA with higher homology may be efficiently obtained at higher temperature under these conditions. However, several factors are thought to influence the stringency of hybridization, such as temperatures and salt concentrations, and one skilled in the art can suitably select these factors to accomplish a similar stringency. More guidelines for the hybridization condition are available in the art, for example, in a reference by Sambrook et al. (1989, Molecular Cloning, A Laboratory Manual, Cold Spring Harbor Press, N.Y.) and in unit 2.10 of the reference by Ausubel et al. (1995, Current Protocols in Molecular Biology, John Wiley & Sons, N.Y.).

Also, in lieu of hybridization, it is also possible to isolate functionally equivalent proteins by a gene amplification method, such as PCR, by synthesizing sequences based on the sequence information of the DNA encoding the human "C-NT2RP3001495" protein (SEQ ID NO:1) and using them as primers.

The proteins functionally equivalent to the human "C-NT2RP3001495" proteins encoded by the DNA isolated by the hybridization or gene amplification techniques, usually are highly homologous to the human "C-NT2RP3001495" proteins (SEQ ID NO:2) at the amino acid sequence level. The proteins of the invention include proteins functionally equivalent to the human "C-NT2RP3001495" protein and are highly homologous to the amino acid sequence of SEQ ID NO:2. "Highly homologous" means typically 65% or higher, preferably 75% or higher, more preferably 85% or higher, and even more preferably 95% or higher identity at the amino acid level. Homology between proteins can be detefniinedlaccording to the algorithm described in the literature (Wilbur et al., Proc. Natl. Acad. Sci. USA 80:726-730, 1983).

The proteins of the present invention may have variations in the amino acid sequence, molecular weight, isoelectric point, presence or absence of sugar chains, or form, depending on the cell or host used to produce them or the purification method utilized as described below. Nevertheless, so long as the protein obtained has a function equivalent to the human "C-NT2RP3001495" protein, it is within the scope of the present invention. For example, when the inventive protein is expressed in prokaryotic cells, e.g., *E. coli*, a methionine residue is added at the N-terminus of the original protein. The present invention also includes such proteins.

The proteins of the present invention can be prepared as recombinant proteins or as naturally occurring proteins, using methods commonly known in the art. The recombinant protein can be, for example, prepared as follows. The DNA encoding the protein of this invention (e.g., DNA having the nucleotide sequence of SEQ ID NO:1) is inserted into an appropriate expression vector, and introduced into suitable host cells. Subsequently, the resulting transformants, the host cell inserted with the expression vector; are recovered, extracted and then purified by chromatography utilizing ion exchange, reverse phase, or gel filtration, or by affinity chromatography with a column in which the antibodies against the protein of the present invention are fixed, or by a combination of these columns.

Alternatively, the protein of the invention can be prepared by expressing the protein in host cells (e.g., animal cells or *E. coli*) as a fusion protein with glutathione S transferase protein, or as a recombinant protein with multiple histidine residues. The expressed protein can be purified using a glutathione column or nickel column. Subsequently, if necessary, regions of the fusion protein (apart from the desired protein) can be digested and removed with thrombin, factor Xa, etc.

The natural protein corresponding to the protein of the invention can be isolated by methods well known in the art, for example, by purifying tissue or cell extracts containing a protein of the invention with an affinity column to which the antibody that binds to the protein of the present invention described below is bound. The antibody may be a polyclonal antibody or monoclonal antibody.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2. The invention also includes a polypeptide, or fragment thereof, that differs from the corresponding sequence shown as SEQ ID NO:2. The differences are, preferably, differences or changes at a non-essential residue or a conservative substitution. In one embodiment, the polypeptide includes an amino acid sequence at least about 60% identical to a sequence shown as SEQ ID NO:2, or a fragment thereof. Preferably, the polypeptide is at least 65%, 70%, 75%, 80%, 85%, 90%, 95%, 98%, 99% or more identical to SEQ ID NO:2 and has at least one cell differentiation-related function or activity described herein, e.g., the polypeptide is involved in the maintenance of differentiation of smooth muscle cells. Preferred polypeptide fragments of the invention are at least 10%, preferably at least 20%, 30%, 40%, 50%, 60%, 70%, or more, of the length of the sequence shown as SEQ ID NO:2 and have at least one cell differentiation-related function or activity described herein. Alternatively, the fragment can be merely an immunogenic fragment.

The present invention also includes partial peptides of the proteins of the present invention. The partial peptides of the present invention comprise at least 7 or more amino acids, preferably 8 or more amino acids, more preferably 9 or more amino acids. The partial peptides can be used, for example, for generating antibodies against the protein of the present invention, screening of compounds binding to the protein of the present invention, or screening of promoters or inhibitors for the protein of the present invention. The partial peptides can be used as antagonists or competitive inhibitors for the protein of this invention. The partial peptides of the invention can be produced by genetic engineering, known methods of peptide synthesis, or by digesting the protein of the invention with an appropriate peptidase. For peptide synthesis, for example, solid phase synthesis or liquid phase synthesis may be used.

DNA encoding an inventive protein can be used for the production of the inventive protein in vivo and in vitro as described above; it is also applicable to, for example, gene therapy for diseases caused by the abnormality in the gene encoding the inventive protein and for diseases that can be treated by the inventive protein. Any type of DNA, such as cDNA synthesized from mRNA, genomic DNA or synthetic DNA, can be used so long as the DNA encodes a protein of the present invention. Also so long as they can encode a protein of the present invention, DNAs comprising arbitrary sequences based on the degeneracy of the genetic code are also included.

The DNA of the present invention can be prepared using methods known in the art. For example, a cDNA library can be constructed from the cells expressing the protein of the present invention, and hybridization can be conducted using a part of the DNA sequence of the present invention (for example, SEQ ID NO:1) as a probe. cDNA libraries may be prepared by, for example, the method described in the literature (Sambrook et al., Molecular Cloning, Cold Spring Harbor Laboratory Press, 1989), and also, commercially available ones can be used. Alternatively, the DNA of the present invention can be obtained by preparing the RNA from the cells expressing the protein of the present invention, synthesizing cDNA by reverse transcriptase, synthesizing the oligo-DNAs based on the DNA sequence of the present invention (for example, SEQ ID NO:1), and amplifying the cDNA encoding the protein of the present invention by PCR using the oligonucleotides as primers.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated nucleic acid molecule which is longer than or equivalent in length to the reference sequence, e.g., SEQ ID NO: 1, the comparison is made with the full length of the reference sequence. Where the isolated nucleic acid molecule is shorter that the reference sequence, e.g., shorter than SEQ ID NO: 1, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (PNAS USA 87.2264-2268, 1990), modified as in Karlin and Altschul, PNAS USA 90:5873-5877, 1993). Such an algoritiun is incorporated into the NBLAST and XBLAST programs of Altschul et al. (J. Mol. Biol. 215:403-410, 1990). BLAST nucleotide searches are performed with the NBLAST program, score=100, wordlengith=12. BLAST protein searches are performed with the XBLAST program, score=50, word length=3. To obtain gapped alignment for comparison purposes Gapped-BLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

The nucleotide sequence of the obtained cDNA is determined to find an open reading frame, and thereby the amino acid sequence of the protein of the invention can be obtained. The cDNA obtained may also be used as a probe for screening a genomic library to isolate a genomic DNA.

More specifically, mRNAs may first be prepared from a cell, tissue, or organ in which the protein of the invention is expressed (e.g. tissues such as liver and kidney). Known methods can be used to isolate mRNAs; for instance, total RNA can be prepared by guanidine ultracentrifugation (Chirgwin et al., Biochemistry 18:5294-5299, 1979) or the AGPC method (Chomezynski et al., Anal. Biochem. 162:156-159, 1987). mRNA may then be purified from total RNA using mRNA Purification Kit (Pharmacia) and such; alternatively, mRNA may be directly purified by QuickPrep mRNA Purification Kit (Pharmacia).

The obtained mRNA is used to synthesize cDNA using reverse transcriptase. cDNA may be synthesized by using a kit such as the AMV Reverse Transcriptase First-strand cDNA Synthesis Kit (Seikagaku Kogyo). Alternatively, cDNA may be synthesized and amplified following the 5'-RACE method (Frohman et al., Proc. Natl. Acad. Sci. U.S.A. 85:8998-9002, 1988; Belyavsky et al., Nucleic Acids Res. 17:2919-2932, 1989) which uses primers described herein, the 5'-Ampli FINDER RACE Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA is verified by conventional methods, such as dideoxynucleotide chain termination.

A DNA of the invention may be designed to have a sequence that is expressed more efficiently by taking into account the frequency of codon usage in the host to be used for expression (Grantham et al., Nucleic Acids Res. 9:43-74, 1981). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG).

The DNA of the present invention also include a DNA hybridizing to a DNA consisting of the nucleotide sequence of SEQ ID NO:1 and encoding a protein functionally equivalent to the above-mentioned protein of the present invention. Those skilled in the art can properly select the appropriate hybridization conditions, and specifically the above-mentioned conditions can be used. Under these conditions, the higher the temperature, the higher the homology of the obtained DNA will be. The above-mentioned hybridizing DNA is preferably a naturally occurring DNA, for example, cDNA or chromosomal DNA.

The present invention also provides a vector into which a DNA of the present invention is inserted. The vectors of the present invention are useful for maintaining the DNA of the present invention within host cells or expressing the protein of the invention.

When the *E. coli* is used as a host cell, there is no limitation other than that the vector should have an "ori" to amplify and mass-produce the vector in *E. coli* (e.g., JM109, DH5α, HB101, or XL1Blue), and a marker gene for selecting the transformed *E. coli* (e.g., a drug-resistance gene selected by a drug such as ampicillin, tetracycline, kanamycin, or chloramphenicol). For example, M13-series vectors, pUC-series vectors, pBR322, pBluescript, pCR-Script, and such can be used. pGEM-T, pDIRECT, pT7, and so on can also be used for subcloning and excision of the cDNA as well as the vectors described above. When a vector is used to produce a protein of the present invention, an expression vector is especially useful. The expression vector, for example, to be expressed in *E. coli* should have the above characteristics to be amplified in *E. coli*. When *E. coli*, such as JM109, DH5α, HB101, or XL1 Blue, is used as the host cell, the vector should have a promoter such as lacZ promoter (Ward et al., Nature 341:544-546, 1989; FASEB J. 6:2422-2427, 1992), araB promoter (Better et al., Science 240:1041-1043, 1988), or T7 promoter that can efficiently promote the expression of the desired gene in *E. coli*. Other examples of the vectors are pGEX-5X-1 (Pharmacia), "QIAexpress system" (Qiagen), pEGFP, and pET (for this vector, BL21, a strain expressing T7 RNA polymerase, is preferably used as the host).

Further, the vector may contain a signal sequence for the secretion of polypeptides. The pelB signal sequence (Lei et al., J. Bacteriol. 169:4379, 1987) can be used as a signal sequence for secretion of proteins, when the proteins are intended to be produced in the periplasm of *E. coli*. Introduction of the vector into a host cell can be performed, for example, by the calcium chloride method or electroporation.

In addition to the vectors for *E. coli*, for example, the vector for producing the proteins of this invention may be a mammal-derived expression vector (e.g., pcDNA3 (Invitrogen), pEGF-BOS (Nucleic Acids Res. 18(17):5322, 1990), pEF, and pCDM8), an insect cell-derived expression vector (e.g., "Bac-to-BAC baculovairus expression system" (GibcoBRL) and pBacPAK8), a plant-derived expression vector (e.g., pMH1 and pMH2), an animal virus-derived expression vector (e.g., pHSV, pMV, and pAdexLcw), a retrovirus-derived expression vector (e.g., pZIPneo), an yeast-derived expression vector (e.g., "Pichia Expression Kit" (Invitrogen), pNV11, and SP-Q01), a *Bacillus subtilis*-derived expression vector (e.g., pPL608 and pKTH50).

In order to express proteins in animal cells, such as CHO, COS, and NIH3T3 cells, the vector should have a promoter necessary for expression in such cells, e.g., SV40 promoter (Mulligan et al., Nature 277:108, 1979), MMLV-LTR promoter, EF1α promoter (Mizushima et al., Nucleic Acids Res. 18:5322, 1990), CMV promoter, etc., and more preferably it has a marker gene for selecting transformants (for example, a drug resistance gene selected by a drug (e.g., neomycin, G418, etc.)). Examples of vectors with these characteristics include pMAM, pDR2, pBK-RSV, pBK-CMV, pOPRSV, pOP13, and so on.

The method using CHO cells deficient in nucleic acid synthetic pathways as the host, and incorporating a vector (such as pCHOI) with a DHFR gene that compensates for the deficiency and amplifying the vector with methotrexate (MTX) can be mentioned as an example method for stably expressing a gene and amplifying the copy number in cells. And as a method for transient expression, a method transforming the COS cells, which have the gene for SV40 T antigen on the chromosome, with a vector (such as pcDNA3) having the SV40 replication origin can be mentioned. The origin used for replication may be those of polyomavirus, adenovirus, bovine papilloma virus (BPV), and the like. In addition, the expression vector may include a selection marker gene for amplification of the gene copies in host cells. Examples of such markers include, but are not limited to, the aminoglycoside transferase (APH) gene, the thymidine kinase (TK) gene, the *E. coli* xanthine-guanine phosphoribosyl transferase (Ecogpt) gene, and the dihydrofolate reductase (dhfr) gene.

The DNA of the present invention can be expressed in animals by, for example, inserting a DNA of the invention into an appropriate vector and introducing the vector into a living body by the retrovirus method, liposome method, cationic liposome method, adenovirus method, and so on. Thus, gene therapy can be conducted for diseases caused by mutations in the "C-NT2RP3001495" gene of this invention. The vectors used include, but are not limited to, adenoviral vectors (e.g., pAdexlcw) and retroviral vectors (e.g., pZIPneo). General techniques for gene manipulation, such as insertion of the DNA of the invention into a vector, can be performed according to conventional methods (Molecular Cloning, 5.61-5.63). The DNA of this invention can be administered to the living body by an ex vivo method or in vivo method.

The present invention also provides a host cell into which the vector of the present invention has been introduced. The host cell into which the vector of the invention is introduced is not particularly limited. *E. coli* and various animal cells can be used. The host cell of this invention can be used as, for example, a production system for producing or expressing the protein of the invention. The production system for producing a protein of the invention may be both in vitro or in vivo production system. For in vitro production, eukaryotic cells or prokaryotic cells can be used.

Useful eukaryotic host cells may be animal, plant, or fungi cells. As animal cells, mammalian cells such as CHO (J. Exp. Med. 108:945, 1995), COS, 3T3, myeloma, baby hamster kidney (BHK), HeLa, or Vero cells, amphibian cells such as *Xenopus oocytes* (Valle et al. Nature 291:340-358, 1981), or insect cells such as Sf9, Sf21, or Tn5 cells can be used. CHO cells lacking DHFR gene (dhfr-CHO) (Proc. Natl. Acad. Sci. U.S.A. 77:4216-4220, 1980) or CHO K-1 (Proc. Natl. Acad. Sci. U.S.A. 60:1275, 1968) may also be used. Among the animal cells, CHO cells are particularly preferable for high-level expression. The vector can be introduced into the host cell by, for example, the calcium phosphate method, the DEAE-dextran method, cationic liposome DOTAP (Boehringer Mannheim) method, electroporation, lipofection, etc.

As plant cells, for example, plant cells originating from *Nicotiana tabacum* are known as protein production system and may be used as callus cultures. As fungi cells, yeast cells such as *Saccharomyces*, including *Saccharomyces cerevisiae*, or filamentous fungi such as *Aspergillus*, including *Aspergillus niger*, are known.

Useful prokaryotic cells include bacterial cells, such as *E. coli*, for example, JM109, DH5a, and HB101, or *Bacillus subtilis*.

These cells are transformed by a desired DNA, and the resulting transform ants are cultured in vitro to obtain the protein. Transformants can be cultured using known methods. Culture medium such as DMEM, MEM, RPM11640, or IMDM may be used for animal cells. The culture medium can be used with or without serum supplement such as fetal calf serum (FCS). The pH of the culture medium is preferably between about 6 and 8. Cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then are recovered. These animal and plant hosts are included in host cells of the present invention.

Animals to be used for the production system described above include mammals and insects. Mammals such as goat, porcine, sheep, mouse, and bovine may be used (Vicki Glaser, SPECTRUM Biotechnology Applications (1993)). Alternatively, the mammals may be transgenic animals.

For instance, a desired DNA may be prepared as a fusion gene, fused with a gene such as goat β casein gene which encodes a protein specifically produced into milk. DNA fragments comprising the fusion gene are injected into goat embryos, which are then transplanted back to female goats. Proteins of interest can be recovered from milk produced by the transgenic goats (i.e., those born from the goats that had received the embryos) or from their offspring. To increase the amount of milk containing the proteins produced by transgenic goats, hormones may be appropriately administered to them (Ebert et al., Bio/Technology 12:699-702, 1994).

Alternatively, insects, such as the silkworm, may be used. Baculoviruses into which the DNA encoding the protein of interest is inserted can be used to infect silkworms, and the desired protein can be recovered from their body fluid (Susumu et al., Nature 315:592-594, 1985).

As plants, for example, tobacco can be used. In use of tobacco, DNA encoding the protein of interest may be inserted into a plant expression vector, such as pMON530, which is introduced into bacteria, such as *Agrobacterium tumefaciens*. Then the bacteria is used to infect tobacco, such as *Nicotiana tabacum*, and a desired polypeptide can be recovered from their leaves (Julian et al., Eur. J. Immunol. 24:131-138, 1994).

A protein of the present invention obtained as above may be isolated from inside or outside of the host cells (e.g., culture media), and purified as a substantially pure homogeneous protein. The method for protein isolation and purification is not limited to any specific method; in fact, any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, recrystallization, and so on may be appropriately selected and combined to isolate and purify the protein.

For example, affinity chromatography, ion-exchange chromatography, hydrophobic chromatography, gel filtration, reverse phase chromatography, adsorption chromatography, and such may be used for chromatography (Daniel R. Marshak et al., Strategies for Protein Purification and Characterization: A Laboratory Course Manual. Ed., Cold Spring Harbor Laboratory Press, 1996). These chromatographies may be performed by liquid chromatography such as HPLC and FPLC. Thus, the present invention includes highly purified proteins, purified by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and so on.

The present invention also provides antibodies that bind to the protein of the invention. The antibody of the invention may take any form, including monoclonal antibody, as well as polyclonal antibodies. Furthermore, antiserum obtained by immunizing an animal such as rabbit with the protein of the invention, all classes of polyclonal and monoclonal antibodies, human antibodies, and humanized antibodies produced by genetic recombination are included.

A protein of the invention used as the antigen to obtain antibodies may be derived from any animal species, but preferably it is derived from a mammal, such as a human, mouse, or rat, and more preferably from human. A human-derived protein may be obtained from the nucleotide or amino acid sequences disclosed herein.

Herein, a protein used as an antigen may be a complete protein or partial peptides thereof. A partial peptide may be, for example, an amino (N)-terminal or carboxy (C)-terminal fragment of the protein. Herein, an antibody is defined as an antibody that reacts with either the full-length or a fragment of the protein.

A gene encoding a protein of the invention or its fragment may be inserted into a known expression vector, which is used to transform a host cell as described herein. The desired protein or its fragment may be recovered from the outside or inside of the host cell by any standard method, and may be used as an antigen. Alternatively, cells expressing the protein or their lysates, or a chemically synthesized protein may be used as an antigen. Short peptides are preferably used as antigens by appropriately combining them with carrier proteins such as keyhole limpet hemocyanin, bovine serum albumin, and ovalbumin.

Any mammalian animal may be immunized with the antigen, but preferably the compatibility with parental cells used for cell fusion is taken into account. In general, animals of Rodentia, Lagomorpha, or Primates are used.

Animals of Rodentia include, for example, mouse, rat, and hamster. Animals of Lagomorpha include, for example, rabbit. Animals of Primates include, for example, a monkey of Catarrhini (old world monkey) such as crab-eating monkey, rhesus monkey, sacred baboon, or chimpanzee.

Methods for immunizing animals with antigens are known in the art. For instance, intraperitoneal injection or subcutaneous injection of antigens is used as a standard method for immunization of mammals. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into emulsion, and then administered to mammals. Preferably, it is followed by several administrations of antigen mixed with an appropriately amount of Freund's incomplete adjuvant every 4 to 21 days. An appropriate carrier may also be used for immunization. After immunization as above, serum is examined for increase of the amount of desired antibodies by a standard method.

Polyclonal antibodies against the proteins of the present invention may be prepared by collecting blood from the immunized mammal examined for the increase of desired antibodies in the serum, and by separating serum from the blood by any conventional method. Serum containing the polyclonal antibodies, or if necessary, a fraction containing the polyclonal antibodies may be isolated from the serum to be used as the polyclonal antibodies of the present invention. For example, immunoglobulin G or M can be prepared by using an affinity column coupled with the protein of the invention to obtain the fraction exclusively recognizing the protein of the invention, and then, purifying the fraction by using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. The other parent cell which is fused with the above immune cell is preferably a mammalian myeloma cell, and more preferably a myeloma cell that has acquired a special feature that can be used for selection of fusion cells by drugs.

Cell fusion of the above immune cell and myeloma cell may be performed by any standard method, such as those described in the literature (Galfre et al., Methods Enzymol. 73:3-46, 1981).

Hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, except desired hybridoma (non-fused cells), to die. Then, the standard limiting dilution is performed to screen and clone a hybridoma cell producing the desired antibody.

Besides the above method, in which a nonhuman animal is immunized with an antigen for preparing hybridoma, human lymphocytes such as that infected by EB virus may be immunized with a protein, protein expressing cells, or their lysates in vitro. Then, the immunized lymphocytes are fused with human-derived myeloma cells that is capable of indefinitely dividing, such as U266, to yield a hybridoma producing a desired human antibody, able to bind to the protein can be obtained (Unexamined Published Japanese Patent Application (JP-A) No. Sho 63-17688).

Subsequently, the hybridomas thus obtained are transplanted into the abdominal cavity of a mouse from which the ascites is collected. The monoclonal antibodies thus obtained can be purified by, for example, ammonium sulfate precipitation or by column chromatography using a protein A or protein G column, a DEAE ion exchange column, an affinity column to which the protein of the invention is coupled, and such. The antibody of the invention can be used not only for purifying and detecting the protein of the invention, but also as a candidate for an agonist or antagonist to the protein of the present invention. It is also expected to use the antibody for antibody therapy of diseases associated with the protein of this invention. When the antibody obtained is administered to the human body (antibody therapy), human antibodies or humanized antibodies are preferred to reduce immunogenicity.

For example, transgenic animals having a repertory of human antibody genes may be immunized with a protein, protein expressing cells, or their lysates as an antigen. Antibody producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can also be recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). A DNA encoding an antibody may be cloned from an immune cell, such as hybridomas or immunized lymphocytes producing the antibody; inserted into an appropriate vector; and introduced into host cells to prepare a recombinant antibody. The present invention also includes recombinant antibodies prepared as described above.

The antibody of the present invention may be a fragment of an antibody or modified antibody, so long as it binds to the protein of the invention. For instance, the antibody fragment may be Fab, F(ab')$_2$, Fv, or single chain Fv (scFv), in which Fv fragments from H and L chains are ligated by an appropriate linker (Huston et al., Proc. Natl. Acad. Sci. U.S.A. 85:5879-5883, 1988). More specifically, an antibody fragment may be generated by treating an antibody with an enzyme such as papain or pepsin. Alternatively, a gene encoding the antibody fragment may be constructed; inserted into an expression vector; and expressed in an appropriate host cell (see, for example, Co et al., J. Immunol. 152:2968-2976, 1994; Better et al., Methods Enzymol. 178:476-496, 1989; Pluckthun et al., Methods Enzymol. 178:497-515, 1989; Lamoyi, Methods Enzymol. 121:652-663, 1986; Rousseaux et al., Methods Enzymol. 121:663-669, 1986; Bird et al., Trends Biotechnol. 9:132-137, 1991).

An antibody may be modified by conjugation with a variety of molecules, such as polyethylene glycol (PEG). The antibody of the present invention includes such modified antibodies. A modified antibody can be obtained by chemically modifying an antibody. These modification methods have been already established in the field.

Alternatively, the antibody of the present invention may be obtained as a chimeric antibody, between a variable region derived from nonhuman antibody and the constant region derived from human antibody, or as a humanized antibody, comprising the complementarity determining region (CDR) derived from-nonhuman antibody, the framework region (FR) derived from human antibody, and the constant region. Such antibodies can be prepared by using known technology.

Obtained antibodies may be purified to homogeneity. The antibodies can be separated and purified by using standard methods for protein separation and purification. For instance, column chromatography such as affinity chromatography, filter, ultrafiltration, salt precipitation, dialysis, SDS-polyacrylamide gel electrophoresis, isoelectric point electrophoresis, and so on may be appropriately selected and combined to isolate and purify the antibody (Antibodies: A Laboratory Manual. Ed Harlow and David Lane, Cold Spring Harbor Laboratory, 1988), but methods are not limited to them. The concentration of the antibody obtained as described above can be determined by the measurement of absorbance, enzyme-linked immunosorbent assay (ELISA), or others.

Columns for affinity chromatography include protein A column and protein G column. For example, protein A column includes Hyper D, POROS, Sepharose F. F. (Pharmacia) and the like.

In addition to affinity chromatography, chromatographic methods include, for example, ion exchange chromatography, hydrophobic chromatography, gel filtration, reverse-phase chromatography, adsorption chromatography and others ("Strategies for Protein Purification and Characterization: A Laboratory Course Manual" Ed Daniel R. Marshak et al., Cold Spring Harbor Laboratory Press, 1996). These chromatographic methods can be conducted by using liquid chromatography such as HPLC and FPLC.

For example, absorbance measurement, enzyme-linked immunosorbent assay (ELISA), enzyme immunoassay (EIA), radioimmunoassay (RIA), or immunofluorescence may be used to measure the antigen binding activity of the antibody of the invention. In ELISA, the antibody of the present invention is immobilized on a plate; the protein of the invention is applied to the plate; and then a sample containing a desired antibody, such as culture; supernatant of antibody producing cells or purified antibodies, is applied. Then, a secondary antibody that recognizes the primary antibody and which is labeled with an enzyme such as alkaline phosphatase is applied, and the plate is incubated. After washing, an enzyme substrate, such as p-nitrophenyl phosphate, is added to the plate, and the absorbance is measured to evaluate the antigen binding activity of the sample. A fragment of the protein, such as a C-terminal fragment, may be used as a protein. BIAcore (Pharmacia) may be used to evaluate the activity of the antibody according to the present invention.

The above methods allow for the detection or measurement of the protein of the invention, by exposing the antibody of the invention to a sample assumed to contain the protein of the invention, and detecting or measuring the immune complex formed by the antibody and the protein. Because the method of detection or measurement of the protein according to the invention can specifically detect or measure a protein, the method may be useful in a variety of experiments in which the protein is used.

The present invention also provides a polynucleotide containing at least 15 nucleotides complementary to the DNA (SEQ ID NO:1) encoding the human protein "C-NT2RP3001495" or the complementary strand thereof.

Herein, the term "complementary strand" is defined as one strand of a double strand DNA composed of A:T and G:C base pair to the other strand. Also, "complementary" is defined as not only those completely matching within a continuous region of at least 15 nucleotides, but also having a homology of at least 70%, favorably 80% or higher, more favorably 90% or higher, and most favorably 95% or higher within that region. The homology may be determined using the algorithm described herein.

Such a nucleic acid includes probes and primers used for the detection and amplification of DNA encoding the inventive protein; probes and primers used for the detection of expression of the DNA; and nucleotide and nucleotide derivatives (e.g., antisense oligonucleotide and ribozyme, or DNAs encoding them, etc.) used for the regulation of expression of the inventive protein. In addition, such a nucleic acid can also be used for the preparation of DNA chip.

When used as primers, such nucleic acids are complementary at the 3' end, and restriction enzyme recognition sequences or tags can be added to the 5' end.

The antisense oligonucleotides include, for example, antisense oligonucleotides hybridizing to any region of the nucleotide sequence of SEQ ID NO:1. The antisense oligonucleotide is preferably an antisense of a continuous sequence of a length of 15 nucleotides or longer within the nucleotide sequence of SEQ ID NO:1. More preferably, the above continuous sequence of a length of 15 nucleotides or longer contains the translation initiation codon.

A derivative or modified form of antisense oligonucleotide may also be used. The modified antisense oligonucleotides may be those modified with lower alkylphosphonate such as methylphosphonate and ethylphosphonate; phosphorothioate; phosphoroamidate; and so on.

Herein, an antisense oligonucleotide is not restricted to those in which all nucleotides are complementary to the corresponding nucleotides within a given region of a DNA or mRNA; so long as it can specifically hybridize with the nucleotide sequences of SEQ ID NO:1, it may have one or more nucleotide mismatches.

A derivative of the antisense oligonucleotide of the present invention may act on cells producing the protein of the invention and may bind to a DNA or mRNA encoding the protein, whereby inhibiting the expression of the protein of the invention by inhibiting its transcription or translation, or by promoting the degradation of mRNA, and thereby inhibiting the function of the protein of the invention.

A derivative of the antisense oligonucleotide of the present invention may be mixed with appropriate carriers which are inactive against the derivative, and may be used as a medicine for externally application such as salve or poultice.

If necessary, it may be mixed with an excipient, isotonizing agent, solubilizing agent, stabilizer, preservative, pain-killer, or the like, and prepared as a tablet, powder, granule, capsule, liposome capsule, injectable solution, liquid formulation, nose drops, freeze-dried agent, etc. The above may be achieved according to standard methods.

For treating patients, a derivative of an antisense oligonucleotide of the present invention may be, for example, directly applied to the affected area of a patient, or administered into blood vessels so as to finally reach the affected area. Moreover, the derivative may be encapsulated in antisense-encapsulating materials such as liposome, poly-L-lysine, lipid, cholesterol, lipofectin, or their derivative in order to increase durability and/or membrane permeability.

Dose of the derivative of the antisense oligonucleotide of the present invention may be appropriately adjusted depending on the patient's conditions, and a favorable amount such as 0.1 to 100 mg/kg, or more preferably 0.1 to 50 mg/kg may be administered.

As the antisense oligonucleotides of the present invention inhibit expression of the protein of the invention, they find utility as inhibitors of the biological activity of the protein of the invention. An inhibitor of expression comprising the antisense oligonucleotide of the present invention is useful because it can inhibit the biological activity of the protein of the invention.

The protein of the invention may be used to screen for compounds that bind to the protein of the present invention. Specifically, the protein may be used in methods of screening for compounds, which method comprises the steps of exposing the protein of the present invention to a test sample in which a compound binding to the protein is expected to be contained; and selecting the compound having the activity of binding to the protein.

The proteins of the invention used for screening may be recombinant or natural proteins, or partial peptides. Alternatively, they may be expressed on the surface of cells or in the form of a membrane fraction. There is no particular restriction on the test sample as it includes, for example, cell extract, cell culture supernatant, product of fermentation microorganism, extract from marine organism, extract from plant, purified or crude protein, peptide, non-peptide compound, synthetic low-molecular-weight compound, natural compound, etc. The inventive protein to be contacted with a test sample can be contacted with the test sample, for example, as a purified protein, as a soluble protein, in a form of protein immobilized on carriers, as a fusion protein with other proteins, in a form of protein presented on cell membrane, as a membrane fraction.

Many methods known to those skilled in the art can be used to screen proteins capable of binding to the inventive protein. Such screening can be carried out, for example, by the immunoprecipitation method. Specifically, the method can be carried out as follows. The gene encoding a protein of this invention is expressed by inserting the gene into a vector for foreign gene expression in pSV2neo, pcDNA I, pCD8, and such, and expressing the gene in animal cells, etc. Any generally used promoters may be employed for the expression, including the SV40 early promoter (Rigby In Williamson (ed.), Genetic Engineering, Vol. 3. Academic Press, London, p.83-141 (1982)), EF-1 α promoter (Kim et al., Gene 91:217-223, 1990), CAG promoter (Niwa et al., Gene 108:193-200, 1991), RSV LTR promoter (Cullen, Methods in Enzymology 152:684-704, 1987), SR α promoter (Takebe et al., Mol. Cell. Biol. 8:466, 1988), CMV immediate early promoter (Seed et al., Proc. Natl. Acad. Sci. U.S.A. 84:3365-3369, 1987), SV40 late promoter (Gheysen et al., J. Mol. Appl. Genet. 1:385-394, 1982), Adenovirus late promoter (Kaufman et al., Mol. Cell. Biol. 9:946, 1989), HSV TK promoter, etc.

Transfer of a foreign gene into animal cells for its expression can be performed by any of the following methods, including the electroporation method (Chu et al., Nucl. Acid Res. 15:1311-1326, 1987), the calcium phosphate method (Chen et al., Mol. Cell. Biol. 7:2745-2752, 1987), the DEAE dextran method (Lopata et al., Nucl. Acids Res. 12:5707-5717, 1984; Sussman et al., Mol. Cell. Biol. 4:1642-1643, 1985), the lipofectin method (Derijard, Cell. 7:1025-1037, 1994; Lamb et al., Nature Genetics 5:22-30, 1993; Rabindran et al., Science 259:230-234, 1993), etc.

The protein of this invention can be expressed as a fusion protein having a recognition site for a monoclonal antibody by introducing the recognition site (epitope) for the monoclonal antibody, the specificity of which has been established, into the N- or C-terminus of the protein of this invention. For this purpose, commercial epitope-antibody systems can be utilized (Igaku, Experimental Medicine 13:85-90, 1995). Vectors which can express fusion proteins with the β-galactosidase, maltose-binding protein, glutathione S-transferase, green fluorescence protein (GFP), and such, via the multicloning site are commercially available.

There is also a report that a fusion protein may be prepared by introducing only small epitope portions consisting of several to a dozen amino acid residues so as not to change the property of the protein of the present invention by the fusion. For example, epitopes such as polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), and such, and monoclonal antibodies to recognize them can be utilized as the epitope-antibody system for screening proteins binding to the protein of this invention (Igaku, Experimental Medicine 13:85-90, 1995).

In immunoprecipitation, immune complexes are formed by adding these antibodies to the cell lysate prepared using suitable surfactants. The immune complex comprises a protein of this invention, a protein comprising the binding ability with the protein, and an antibody. Immunoprecipitation can be also performed by using antibodies against a protein of this invention, besides using antibodies against the above-described epitopes. An antibody to a protein of this invention can be prepared, for example, by inserting a gene encoding the protein of the invention into an appropriate expression vector of *E. coli* to express it in the bacterium, purifying the expressed protein, and immunizing rabbits, mice, rats, goats, chicken, and such against the purified protein. The antibody can be also prepared by immunizing the above-described animals against synthetic partial peptides of the protein of the present invention.

Immune complexes can be precipitated using, for example, Protein A Sepharose and Protein G Sepharose when the antibody is a murine IgG antibody. In addition, if a protein of this invention is prepared as a fission protein with the epitope, such as GST, an immune complex can be formed by using a substance specifically binding to these epitopes, such as glutathione-Sepharose 4B, in the same mannere as in the use of the antibody against the protein of the present invention.

Immune precipitation, in general, may be carried out according to, or following the method described in the literature (Harlow, E. and Lane, D.: Antibodies, pp. 511-552, Cold Spring Harbor Laboratory publications, New York (1988)).

SDS-PAGE is generally used for the analysis of immunoprecipitated proteins. Bound proteins can be analyzed based on the molecular weights of proteins using a gel of an appropriate concentration. In this case, although proteins bound to a protein of this invention, in general, are hardly detectable by the usual protein staining method, such as Coomassie staining and silver staining, the detection sensitivity can be improved by culturing cells in a medium containing radioisotopes, such as $^{35}$S-methionine and $^{35}$S-cysteine, to label proteins inside the cells, and detecting the labeled proteins. Once the molecular weight of the protein is determined, the desired protein can be purified directly from the SDS-polyacrylamide gel and can be sequenced.

In addition, proteins binding to a protein of this invention can be isolated using the West-western blotting method (Skolnik et al., Cell 65:83 -90, 1991) with the protein of this invention. Namely, cDNA is isolated from cells, tissues, and organs, in which the protein binding to a protein of this invention is expected to be expressed (e.g. liver and kidney), and transferred into a phage vector (for example, λgt11, ZAP, and such) to prepare a cDNA library, which is then expressed on LB-agarose plates. The protein thus expressed is fixed on a filter; reacted with the labeled, purified protein of this invention; and plaques expressing a protein bound to a protein of this invention can be detected by the label. Methods for labeling the proteins of this invention include methods using the binding activity of biotin and avidin; methods using antibodies specifically binding to the proteins of this invention, or peptides or polypeptides fused with the protein of this invention (e.g., GST); methods using the radioisotopes; methods using fluorescence; etc.

Alternatively, in another embodiment of the method for screening of the present invention, the two-hybrid system utilizing cells may be used (Fields et al., Trends Genet. 10:286-292, 1994; Dalton et al., Cell 68:597-612, 1992; "MATCHMAKER two-Hybrid System", "Mammalian MATCHMAKER Two-Hybrid Assay Kit", "MATCHMAKER One-Hybrid System (all from Clontech), "HybriZAP Two-Hybrid Vector System" (Stratagene)). In the two-hybrid system, an inventive protein or a partial peptide thereof is fused with the SRF DNA-binding region or GAL4 DNA-binding region, and then is expressed in yeast cells; a cDNA library, which express proteins in the form of fusion protein with the VP16 or GAL4 transcription activation region, is prepared from cells that are predicted to express a protein binding to an inventive protein; the resulting cDNA library is introduced into the above-mentioned yeast cells; and then a cDNA derived from the library is isolated from a detected positive clone (when a protein binding to the inventive protein is expressed in yeast cells, the reporter gene is activated by the binding of the two proteins, and thus positive clones are detectable). A protein encoded by the cDNA can be prepared after the isolated cDNA is introduced and expressed in E. coli. Thus it is possible to prepare a protein binding to an inventive protein or the encoding gene. Reporter genes to be used in the two-hybrid system include, but are not limited to, for example, Ade2 gene, LacZ gene, CAT gene, luciferase gene, PAI-1 (Plasminogen activator inhibitor type1) gene in addition to HIS3 gene. The screening by the two-hybrid method can be conduced by using mammalian cells or others in addition to yeast.

Compounds binding to a protein of the present invention can be screened by affinity chromatography. For example, a protein of the invention is immobilized on a carrier of an affinity column, and a test sample, in which a protein binding to the protein of the invention is supposed to be expressed, is applied to the column. A test sample herein may be, for example, cell extracts, cell lysates, etc. After loading the test sample, the column is washed, and proteins bound to a protein of the invention can be prepared.

The amino acid sequence of the resulting protein is then analyzed. Based on the result, an oligo-DNA is synthesized and used as the probe to screen a cDNA library. This can provide a DNA encoding the protein.

In the present invention, a biosensor on the basis of surface plasmon resonance phenomenon can be used as a means to detect or assay the bound compounds. By utilizing the biosensor on the basis of surface plasmon resonance phenomenon, the interaction between the inventive protein and a test compound can be observed as a surface plasmon resonance signal in real time using a small amount of protein without labeling (e.g., BIAcore, Pharmacia). Thus the binding between the inventive protein and the test compound can be assessed by using biosensor of BIAcore, or the like.

In addition, methods are known in the art for isolating compounds binding to a protein of the invention, which are not limited only to proteins (including agonists and antagonists). Such methods include, for example, the method of screening for a molecule binding to a protein of the invention by contacting a synthetic compound or natural substance bank, or a random phage peptide display library with an immobilized protein of the invention, and the high-throughput screening method using a combinatorial chemistry technique (Wrighton et al., Science 273:458-64, 1996; Verdine G. L., Nature 384:11-13, 1996; Hogan J. C. Jr., Nature 384:17-9, 1996).

Compounds isolated by the screening of this invention are candidates for agents to regulate the activity of a protein of this invention, and thought to be applied to treatments for disorders caused by expressional and functional abnormalities, and such of the protein, and diseases which can be treated by controlling the activity of the protein. Compounds which can be obtained by the screening method of this invention, the partial structure of which is modified by addition, deletion and/or substitution, are also included in the compounds binding to the protein of this invention.

When a protein of this invention or compounds isolated by the screening of this invention are used as drugs for humans and other animals, for example, mice, rats, guinea pigs, rabbits, chickens, cats, dogs, sheep, pigs, cattle, monkeys, baboons, and chimpanzees, they can be administered by directly administering the protein or isolated compound itself to a patient or by administering it after formulated according to known pharmaceutical methods. They can be administered, as the occasion demands, for example, orally, as sugar-coated tablets, capsules, elixirs and microcapsules, or parenterally, in the form of sterile solutions in water or other pharmaceutically acceptable liquids, or suspensions for injections. For example, they may be formulated by appropriately mixing with pharmaceutically acceptable carriers or media, specifically sterile water, physiological saline, plant oil, emulsifying agents, suspending agents, surfactants, stabilizers, seasonings, excipients, vehicles, anticeptics, binders, and such, in the unit dosage form required in a generally accepted pharmaceutical procedure. Amounts of effective ingredients in these pharmaceutical preparations are adjusted so as to obtain the appropriate dose in the specified range.

Additives which can be mixed in tablets and capsules include, for example, binders such as gelatin, corn starch, tragacanth gum and arabic gum; excipients such as crystalline cellulose; bulking agents such as corn starch, gelatin and alginic acid; lubricants such as magnesium stearate; sweetening agents such as sucrose, lactose or saccharine; and flavors such as peppermint, *Gaultheria adenothrix* oil or cherry. When the dispensing unit form is a capsule, liquid carriers, such as oil, can be further added to the above-described materials. Sterile compositions for injection can be prescribed using vehicles such as distilled water for injection according to standard pharmaceutical procedure.

Aqueous solutions for injections include, for example, physiological saline, and isotonic solutions containing: glucose and other supplements such as D-sorbitol, D-mannose, D-mannitol, sodium chloride, and such; and suitable solubilizers, for example, alcohols, more specifically, ethanol, polyalcohols such as propylene glycol, polyethylene glycol, nonionic surfactants such as Polysorbate 80 (TM) and HCO-50 may be used together.

Oily solutions, including sesame oil and soybean oil, and benzyl benzoate and benzyl alcohol may be used together as the solubilizer. Injections may be combined with buffers such as phosphate buffer and sodium acetate buffer; soothing agents such as procaine hydrochloride; stabilizers such as benzyl alcohol, phenols and antioxidants. Injections thus prepared are typically filled in suitable ampules.

The administration to patients is done by methods commonly known to those skilled in the art, such as intraarterial, intravenous, or subcutaneous injections, as well as intranasal, bronchial, intramuscular, percutaneous, or oral administrations. One skilled in the art can suitably select the dosage according to the body-weight or age of a patient, or the method of administration. If the compound can be encoded by DNA, the DNA may be used for gene therapy by incorporating the DNA into a vector for gene therapy. Dosages and administration methods vary depending on the body-weight, age, symptoms, and such of patients, but those skilled in the art can appropriately select them.

Although the specific dosage of the protein of the invention changes according to the subject to be treated, the target organs, symptoms, and administration methods, it is generally considered to be, for example, about 100 µg to 20 mg one day for an adult (as body-weight 60 kg) in the form of injections.

Though they vary depending on the symptoms, doses of compounds binding to a protein of this invention or compounds regulating the activity of such a protein may be generally in the range of about 0.1 to 100 mg, preferably about 1.0 to 50 mg, and more preferably about 1.0 to 20 mg per day for adults (based on the body weight 60 kg) in the case of oral administration.

Though it varies depending on the subject to be administered, target organ, symptom and method of administration, a single dose of the compounds for the parenteral administration is thought to be preferably administered, for example, when it is in the form of injection, intravenously to normal adults (based on the body weight 60 kg) in the range of about 0.01 to 30 mg, preferably about 0.1 to 20 mg, and more preferably about 0.1 to 10 mg or thereabout per day. Doses converted on the 60 kg body weight basis or the body surface area can be similarly administered to other animals.

All publications and patents cited herein are incorporated by reference in their entirety.

DETAILED DESCRIPTION

Figure 1:
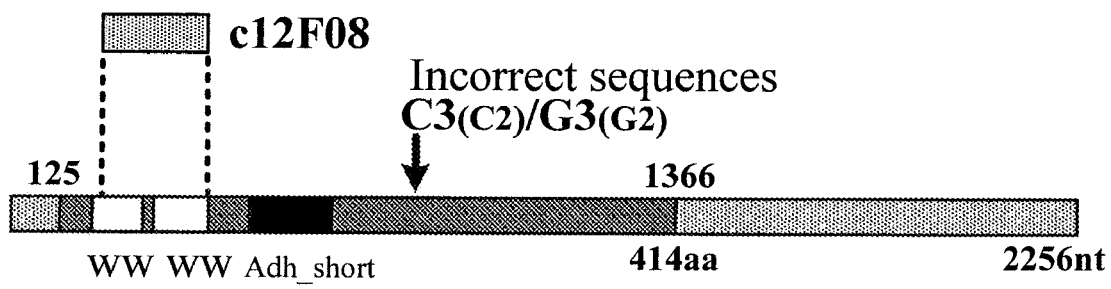
FIG. 1 is a schematic diagram showing the structural features of the amino acid sequences of human "C-NT2RP3001495" of the invention, chicken "12F08" and "HHCMA56". The protein "C-NT2RP3001495" of the present invention contains WW domains and Adh short motif in the N-terminal region.

The invention is illustrated more specifically with reference to the following examples, but is not to be construed as being limited thereto.

EXAMPLE 1

Construction of a cDNA Library by the Oligo-capping Method

The NT-2 neuron progenitor cells (Stratagene), teratocarcinoma cells from human fetal testis, which can be differentiated into neurons by the treatment with retinoic acid were cultured for two weeks after induction treatment by the addition of retinoic acid according to the manufacturer's instructions.

After the culture, the cells were collected, and mRNA was extracted according to the method described in the literature (Sambrook et al., Molecular Cloning Second edition, Cold Spring harbor Laboratory Press 1989). Then, poly(A)$^+$ RNA was purified by using oligo dT cellulose.

This poly(A)$^+$ RNA was used to construct a cDNA library by the oligo-capping method (Maruyama et al., Gene, 138: 171-174, 1994). Using the Oligo-cap linker (agcaucgagu cggccuuguu ggccuacugg/SEQ ID NO:5) and the Oligo-dT primer (gcggctgaag acggcctatg tggccttttt tttttttt tt/SEQ ID NO:6), bacterial alkaline phosphatase (BAP) treatment, tobacco acid phosphatase (TAP) treatment, RNA ligation, the first strand cDNA synthesis, and removal of RNA were performed according to the references (Suzuki et al., Protein, Nucleic acid and Enzyme 41:197-201, 1996; Suzuki et al., Gene 200:149-156, 1997). Then, 5'- and 3'-PCR primers (agcatcgagt cggccttgtt g/SEQ ID NO:7, and gcggctgaag acggcctatg t/SEQ ID NO:8, respectively) were used for performing PCR to convert the cDNA into double stranded cDNA, which was then digested with SfiI. Then, the DraIII-cleaved pME18SFL3 (GenBank AB009864, expression vector) was used for cloning the cDNA in a unidirectional manner, and cDNA libraries were obtained. The nucleotide sequence of the 5'- and 3'-ends of the cDNA clones was analyzed with a DNA sequencer (ABI PRISM 377, PE Biosystems) after sequencing reactions performed with the DNA sequencing reagents (Dye Terminator Cycle Sequencing FS Ready Reaction Kit, dRhodamine Terminator Cycle Sequencing FS Ready Reaction Kit, or BigDye Terminator Cycle Sequencing FS Ready Reaction Kit, PE Biosystems), according to the instructions.

pME18SFL3 vector contains the SRα promoter and SV40 small t intron in the upstream, as well as the SV40 polyA addition signal sequence downstream of the cloning site, respectively. As the cloning site of pME18SFL3 has asymmetrical DraIII sites, and the ends of cDNA fragments contain SfiI sites complementary to the DraIII sites, the cloned cDNA fragments can be unidirectionally inserted downstream of the SRα promoter. Therefore, clones containing full-length cDNA can be expressed transiently by introducing the obtained plasmid directly into COS cells. Thus, the clones can be analyzed very easily in terms of the proteins that are the gene products of the clones, or in terms of the biological activities of the proteins.

EXAMPLE 2

Estimation of the Completeness at the 5'-ends of the Clones Contained in the cDNA Libraries Constructed by the Oligo-capping Method The full-length ratio at the 5'-end sequence of respective clones in the human cDNA libraries constructed by the oligo-capping method was determined as follows. The clones whose 5'-end sequences were consistent with those of known human mRNA in the public database were judged to be "full-length" if they had a longer 5'-end sequence than that of the known human mRNA; or even though the 5'-end sequence was shorter, if it contained the translation initiation codon it was judged to have the "full-length" sequence. Clones which did not contain the translation initiation codon were judged to be "not-full-length". The full-length ratio ((the number of full-length clones)/(the number of full-length and not-full-length clones)) at the 5'-end of the cDNA clones from each library was determined by comparing with known human mRNA. As a result, the full-length ratio of the 5'-ends was 63.5%. TIle result indicates that the full-length ratio at the 5'-end sequence was extremely high in the human cDNA clones obtained by the oligo-capping method.

EXAMPLE 3

Assessment of the Full-length Ratio of the 5'-end of the cDNA by the ATGpr and the ESTiMateFL The ATGpr, developed by Salamov A.A., Nishikawa T., and Swindells M.B. in the Helix Research Institute, is a program for prediction of the translation initiation codon based on the characteristics of the sequences in the vicinity of the ATG codon (Salamov et al., Bioinformatics 14:384-390, 1998). The results are shown with expectations (also mentioned as ATGpr1 below) whether the ATG is a true initiation codon (0.05-0.94). When the program was applied to the 5'-end sequences of the clones from the cDNA library that was obtained by the oligo-capping method having 65% full-length ratio, the sensitivity and specificity of the estimation of the full-length clone (clone containing the N-terminus of the ORF) were improved to 82 to 83% by selecting only clones having an ATGpr1 score 0.6 or higher. The maximum ATGpr1 score for 5'-end sequence of NT2RP3001495 was 0.94.

Next, the ESTiMateFL was used for the assessment of the clones. The ESTiMateFL, developed by Nishikawa and Ota in the Helix Research Institute, is a method for selecting clones expected to have a full-length cDNA by comparing with the 5'-end or 3'-end sequences of ESTs in the public database.

By this method, a cDNA clone is judged to be most likely not to be full-length if there exist any ESTs which have longer 5'-end or 3'-end sequences than the clone. The method is systematized for high throughput analysis. A clone is judged to be full-length if the clone has a longer 5'-end sequence than the ESTs in the public database corresponding thereto. Even if a clone has a shorter 5'-end, the clone is judged to be full-length if the difference in length is within 50 bases, and otherwise judged not to be full-length, for convenience.

Those clones whose 5'-end sequence is matching with the known mRNA, about 80% of the clones judged to be full-length by the comparison with ESTs were also judged to be full-length by the assessment of the 5'-end sequence by comparing with known mRNA. Also, about 80% of the clones judged to be not full-length in the 5'-end sequence by comparing with ESTs were also judged to be not full-length in the 5'-end sequence by comparison with known mRNA. The precision of the estimation by comparing with ESTs is improved with increasing numbers of ESTs to be compared. However, in case with limited numbers of ESTs, the reliability becomes low. Thus, the method is effective in excluding clones with high probability of being not-full-length from the cDNA clones that is synthesized by the oligo-capping method having a 5'-end sequence full-length ratio of about 60%. In particular, the ESTiMateFL is efficiently used in estimating the full-length ratio at the 3'-end sequence of cDNA of a human unknown mRNA, a significant number of which are deposited in the public database as EST deposits.

Results of the above assessment for the full-length ratio showed that the clone NT2RP3001495, of which maximal value of ATGpr1 is greater than 0.3, is a novel clone with a high probability of being full-length and also which shares no sequence identity with any of human EST sequences at least either at the 5'-end sequence or 3'-end sequence, or both ends.

EXAMPLE 4

Isolation of cDNA Associated with the Maintenance of Differentiation of Chicken Smooth Muscle Cells New-laid eggs from chicken White Leghorn were incubated at 37° C. in an incubator. The fetuses were taken out after 15-day incubation. The gizzard was resected and placed in a dish containing PBS (phosphate buffer) with forceps. The resected gizzard was cut into small blocks with scissors, and then, was dispersed as individual cells by collagenase treatment. Then, large cell aggregates were removed with a filter of 100 μm. The cells were washed with Dulbecco's modified Eagle's medium (Nissui #05919) containing 20 mg/ml bovine serum albumin (BSA: SigmaA-7638), and the cell count was determined with a hemocytometer. $5 \times 10^4$ cells were plated on a 3.5-cm petri-dish, and were cultured at 37° C. overnight. These culture media were changed with 20 mg/ml BSA/DMEM containing 0.2 ng/ml insulin-like growth factor (IGF-I; Boehringer Mannheim #1048066), and the media were replaced by fresh ones every two days. The concentration of collagenase type-V (SigmaC-9263) was adjusted to 1 mg/ml by using Sol.3 (137 mM NaCl, 5 mM KCl, 4 mM NaHCO$_3$, 5.4 mM Glucose, 2 mM MgCl$_2$, 10 mM PIPES; adjusted to pH6.5), and the collagenase solution was used after sterilization by filtration. On the ninth day of culture the cells were harvested, and then the total RNA was extracted therefrom. The cells cultured with culture medium containing IGF-I are called differentiated smooth muscle cells in the experiments described below, while the cells that had been changed to have a proliferative character by adding bovine serum or anti-IGF-I antibody (Upstate Biotechnology #05-172) at a concentration of 5 μg/ml, are called dedifferentiated smooth muscle cells. The cells were not dedifferentiated by the addition of mouse IgG antibodies (hereinafter referred to as control antibodies), which were not the anti-IGF-I antibody but the subclass of which were the same as that of the anti-IGF-I antibody, and thus, the cells were maintained as the differentiated smooth muscle cells. Complementary DNAs were synthesized from 1 μg of the total RNAs extracted from differentiated cells or dedifferentiated cells of chicken smooth muscle that had been prepared by adding the control antibodies or anti-IGF-I antibodies. The synthesis of the cDNAs was carried out by a method using CapFinede PCR Synthesis Kit (CLONTECH #K1052-1) according to the manual thereof Specifically, total RNAs used were prepared from three types of cells: chicken gizzard smooth muscle cells dedifferentiated by adding neutralizing anti-IGF-I antibodies (hereinafter abbreviated as CGSMC-B); differentiated smooth muscle cells by the addition of 0.2 ng/ml IGF-I and the control antibodies (hereinafter abbreviated as CGSMC-C); and dedifferentiated smooth muscle cells obtained one day after the addition of bovine serum (hereinafter abbreviated as CGSMC-D). A 3.5 µl solution containing 1 µg of total RNA, 1 µl of CDS primer (attached to the kit) and 0.5 µl of CapSwitch II oligo (attached to the kit) were mixed, incubated at 70° C. for 2 minutes, and then was allowed to stand at room temperature. Then, according to the manual attached to the kit, 2 µl of 5× first strand buffer, 1 µl of DTT, 1 µl of 10 mM dNTP and 1 µl of MMLV reverse transcriptase were further added to the mixture, and the resulting mixture was incubated at 42° C. for 1 hour. 40 µl of TE (pH7.5) was added to the mixture, and then the resulting solution was incubated at 72° C. for 7 minutes. A 1-µl aliquot of the resulting cDNA was diluted 10-fold with distilled water, and was used for the PCR as described below. The composition of the reaction mixture was as follows.

Composition of Reaction Mixture:

| | |
|---|---|
| 10 µl | cDNA (10-fold dilution) |
| 10 µl | 10× Advantage KlenTaq buffer |
| 4 µl | 2.5 mM dNTP |
| 2 µl | 10 µM PCR primer (attached to the kit) |
| 2 µl | Advantage KlenTaq mix (50X) |
| 72 µl | distilled water |

0.2-ml PCR tubes containing the above-mentioned reaction components were placed on a Thermal Cycler PE2400 (PE Biosystems) preheated to 95° C. After the denaturation at 95° C. for 1 minute, PCR was conducted with 15 cycles of two steps: 95° C. for 15 seconds and then 68° C. for five minutes. Then, PCR was further continued with the same two-step profile, but a 15-µl aliquot was taken as a sample every 3 cycles. The samples were used to identify the number of cycles where the products by PCR amplification had been increased logarithmically and, at the same time, where the amplification had not been yet saturated. The results showed that the condition of 17 cycles may be reasonable, and thus PCR amplification was conducted under this condition by using 8 tubes for each cDNA. The product of the PCR amplification in 8 tubes for each cDNA were combined together, and then, were deproteinized by mixing with an equal volume of phenol/chloroform/isoamyl alcohol (25:24:1). Then, the solutions were concentrated by n-butanol extraction. The concentrated solutions were subjected to CLONTECH CHROMA SPIN-1000 Column, and then, were eluted according to the manual by using 1× TNE buffer (10 mM Tris-HCl (pH8.0)/10 mM NaCl/0.1 mM EDTA). The subtraction was carried out using the resulting cDNA according to the manual of CLONTECH PCR-Select Subtraction Kit. 2 µg cDNA of CGSMC-B, CGSMC-C or CGSMC-D was digested with 15 units of restriction enzyme RsaI in a total solution volume of 50 µl by using a buffer attached to the kit at 37° C. for 3 hours. 2.5 µl of 20× EDTA/glycogen mix attached to the kit and 3 volumes of SALT solution (attached to the kit) were added to the mixture. The resulting mixture was vigorously mixed, and then 8 µl of PCR-Pure BIND (attached to the kit) was added thereto. The mixed solution was incubated at room temperature for five minutes, and then centrifuged at 14,000 rpm for one minute. The supernatant was removed, and the precipitate was dissolved in 1 ml of WASH Solution (attached to the kit) by pipetting. The solution was again centrifuged at 14,000 rpm for one minute, and the supernatant was removed. Further, the residual WASH Solution was removed completely by repeating centrifugation. After air-drying for 10 minutes, the precipitate was suspended in 17 µl of TE buffer by pipetting, and then the suspension was incubated at room temperature for five minutes while keeping the suspended state of the solution. Then, the solution was centrifuged at 14,0000 rpm for five minutes. The supernatant containing eluted DNA was transferred to a separate tube, and then 9 µl of 4 M ammonium acetate ($NH_4OAc$; attached to the kit) and 75 µl of ethanol were added thereto for ethanol precipitation. The tube was centrifuged for 20 minutes, and the resulting precipitate was washed with 80% ethanol. The precipitate was air-dried for 10 minutes, and then was dissolved in 6.7 µl of 1× TNE buffer. The sample of CGSMC-C, RsaI-digested cDNAs of which concentration was adjusted to 300 ng/µl, was used a tester, and therefore, the sample was further subjected to adapter ligation. The sample of CGSMC-C was incubated for ligation with adapter 1 (10 µM) or adapter 2 (10 µM) (both attached to the kit) by using 1 µl of T4 DNA ligase in a total volume of 10 µl containing Ligation buffer attached to the kit at 16° C. overnight. 1 µl of 20× EDTA/glycogen mix was added to the mixture, and then the enzyme was inactivated by the treatment at 72° C. for five minutes. The resulting adapter-ligated tester cDNAs are called TC-1 and TC-2, respectively.

1.5 µl of each dedifferentiated chicken gizzard smooth muscle cells, CGSMC-B and CGSMC-D (300 ng/µl), which serve as driver cDNA digested with restriction enzyme RsaI, were combined with 1.5 µl of TC-1 and 1.5 µl of 4× Hybridization buffer attached to the kit to a total volume of 6 µl in a 0.2-ml tube. Then, one drop of mineral oil was added thereto, and this is referred to as H1. Similarly, a tube was prepared with TC-2 instead of TC-1, and was named H2. H1 and H2 were heated for denaturation at 98° C. for 90 seconds in a Thermal cycler (PE Biosystems PE2400), and then were incubated at 68° C. for 8 hours. A driver cDNA solution with a total volume of 4 µl was freshly prepared by combining 1.5 µl of dedifferentiated chicken gizzard smooth muscle cells, CGSMC-B and CGSMC-D (300 ng/µl), respectively, digested with restriction enzyme RsaI, and 1 µl of 4× Hybridization buffer attached to the kit. The solution was denatured by heat at 98° C. for 90 seconds. An air bubble was sucked into the 200-µl pipette tip containing H2 to avoid direct contact of the solution with a solution of denatured driver cDNA that was sucked therein later. The solutions were transferred in a tube containing H1, and then were mixed by pipetting. The tube containing H1 was allowed to stand on a Thermal cycler during the manipulation. The tube was incubated at 68° C. overnight to hybridize the tester cDNA to the cDNA in the driver cDNA. 200 µl of Dilution Buffer (attached to the kit) was added and mixed by pipetting, and the resulting mixture was incubated at 75° C. for 7 minutes. This was stored as a diluted subtracted IGF(+) cDNA at −20° C. The diluted subtracted CGSMC IGF(+) cDNA was subjected to primary PCR in a reaction solution containing the following components.

Composition of Reaction Mixture:

| | |
|---|---|
| 16 µl | distilled water |
| 2.5 µl | 10x Advantage KlenTaq PCR buffer |
| 4 µl | 2.5 mM dNTPs (TAKARA) |
| 1 µl | 10 µM PCR primer 1 (attached to the kit) |
| 0.5 µl | 50x Advantage KlenTaq DNA polymerase |
| 1 µl | diluted subtracted CGSMC IGF(+) cDNA |

These components were mixed in a 0.2-ml tube, and one drop of mineral oil was added thereto. After incubation at 75° C. for five minutes, and then at 94° C. for 25 seconds, PCR was conducted with 27 cycles of three steps: 94° C. for 10 seconds, 66° C. for 30 seconds, and 72° C. for 90 seconds. 3 µl of the primary PCR product was diluted with 27 µl of distilled water, and then the following PCR was conducted. Composition of Reaction Mixture:

| | |
|---|---|
| 18.5 µl | distilled water |
| 2.5 µl | 10x Advantage KlenTaq PCR buffer |
| 0.5 µl | 10 mM dNTPs (attached to the kit) |
| 1 µl | 10 µM Nested primer 1 (attached to the kit) |
| 1 µl | 10 µM Nested primer 2 (attached to the kit) |
| 0.5 µl | 50x Advantage KlenTaq DNA polymerase |
| 1 µl | 10 times diluted primary PCR product |

These components were mixed in a 0.2-ml tube, and one drop of mineral oil was added thereto. After incubation at 94° C. for 25 seconds, PCR was conducted with 19 cycles of three steps: 94° C. for 10 seconds, 66° C. for 30 seconds, and 72° C. for 90 seconds. A sample was taken from the tube at cycles 13, 15, 17, and 19, respectively, and then, amplification of PCR products were tested by agarose gel electrophoresis. According to the result, the products seemed to be saturated with more than 15 cycles. Thus, products obtained with 15 cycles of PCR were used to carry out the following experiment. 8 µl out of a total reaction volume of 25 µl was used in the electrophoresis, and the remaining 17 µl was combined with 5 volumes of buffer PB (QIAGEN; buffer attached to Qiaquick PCR purification kit). The resulting solution was mixed well. This was loaded onto Qiaquick column (a component of the same kit as described above), and the column was centrifuged at 13,000 rpm. 750 µl of Buffer PE (a component of the same kit as described above) was added to the column, and then the column was centrifuged again. A fraction (5 µl) eluted with 30 µl of water attached to the kit was used for TA cloning with a pGCEM-T Vector system (A3600) from Promega according to the manual. After ligation at 4° C. overnight, 2 µl of the reaction solution was used for the transformation of *E. coli* DH5α according to the procedure of the kit. The resulting colonies were used for colony PCR using the above-mentioned Nested primer 1 and Nested primer 2. The resulting PCR products were purified by using MultiScreen from Millipore to remove the primers. Then DNA sequence analysis was performed by using respective primers and the Dye Terminator Cycle Sequencing FS Ready Reaction kit (Perkin Elmer; Catalog #402122). The nucleotide sequence of the resulting cDNA fragment was determined, and a sequence named "12F08" (SEQ ID NO:3) was obtained.

EXAMPLE 5

Isolation of Human Novel Gene "C-NT2RP3001495" Having Homology to Chicken "12F08"

NCBI UniGene database was searched for homology to the cDNA fragment "12F08" (SEQ ID NO:3) obtained in Example 4 by NCBI BLASTN2.0. The result showed that the "12F08" sequence exhibited 82% homology to a clone Hs#S1388556 belonging to human Unigene cluster Hs.128045. Considering that the sequence comparison was made between chicken and human, the gene belonging to Unigene cluster Hs.128045 can be concluded to be the human orthologue to chicken 12F08. Then, the following sequences belonging to Hs.128045 were assembled into a contig, and the obtained sequence was named Hs128045_12F08con.

gn1|UG|Hs#S1388556 wb85d11.x1 *Homo sapiens* cDNA, 3' end/clone=IMAGE:2312469/clone_end=3'/gb=AI669330/gi=4834104 gn1|UG|Hs#S1579061 wr85e01.x1 *Homo sapiens* cDNA, 3' end/clone=IMAGE:2494488/clone_end=3'/gb=AI984802/gi=5812079 gn1|UG|Hs#S1008273 op61g03.s1 *Homo sapiens* cDNA, 3' end/clone=IMAGE:1581364/clone_end=3'/gb=AA970236/gi=3145744 gn1|UG|Hs#S984806 o141b06.s1 *Homo sapiens* cDNA, 3' end/clone=IMAGE:1526003/clone_end=3'/gb=AA912726/gi=3052118

The pfam motif database was searched for Hs128045_12F08con using estwisedb of the database search programs Wise2 designed by Ewan Birney at Sanger Center. The result showed that both 12F08 and Hs128045_12F08con contained two WW domains. The WW domain is known to be an important functional domain for protein-protein interaction, and many proteins containing WW domain have been reported.

Then, cDNA sequences of the Helix Research Institute (helix clones; Japanese Patent Application No. Hei 11-248036; Japanese Patent Application No. 2000-118776) were searched using the sequence obtained from the above-mentioned Unigene Cluster as a query. The cDNA sequences of the Helix Research Institute are clones obtained by the method in Examples 1 to 3 which probability of containing a full-length sequence is high.

The homology search using the helix clones revealed that the sequence was identical to that of a helix clone "C-NT2RP3001495". In addition, the gene has been identified to be identical to Hs.519 Human oxidoreductase (HHCMA56) of Unigene as well. However, detailed analysis by using CAP of GCG Packaging software showed that "C-NT2RP3001495" was longer than HHCMA56; the sequence of HHCMA56 started at nucleotide 578 of "C-NT12RP3001495" sequence; the C-residue triplet at nucleotides 276 to 278 in the sequence of HHCMA56 was altered to a C-residue doublet in the sequence of "C-NT2RP3001495"; and further, the G-residue triplet at nucleotides 280 to 282 in the sequence of HHCMA56 was altered to a G-residue doublet at nucleotides 856 to 858 in the sequence of "C-NT2RP3001495". Therefore, PCR amplification was performed using the oligonucleotide, 1495-588U24 (5'-GCA GGA ACA TGG CAA GGG CGA GTG-3'/SEQ ID NO:9), corresponding to the 24 nucleotides starting from nucleotide 588 of "C-NT2RP3001495", and the oligonucleotide, 1495-862L23 (5'-GGG CAG GAG CTG AGC GGC ACA AA-3'/SEQ ID NO:10), having a complementary strand to the 23 nucleotides starting from nucleotide 839 of "C-NT2RP3001495", as well as human genomic DNA (Clontech #6550-1) as the template (pre-heating at 94° C. for 5 minutes; 45 cycles of denaturation at 94° C. for 15 seconds, annealing at 55° C. for 30 seconds, and extension at 72° C. for 30 seconds; final extension at 72° C. for 3 minutes). The resulting DNA was cloned into pGEM-T (Promega; A3600), and the sequence was determined.

As a result, it was revealed that the sequence of "C-NT2RP3001495" was correct, and the sequence of HHCMA56 contained incorrect nucleotides by misreading. Positional relation between the amino sequences encoded by respective genes is shown in FIG. 1. While an adh short motif, which is a motif found in oxidoreductase and dehydrase, is present in HHCMA56, the two WW domains, which are present in "C-NT2RP3001495", are not found in HHCMA56. In addition, because of two nucleotide differences, HHCMA56 has been deposited as a gene encoding a protein consisting of 371 amino acids, which is entirely different from "C-NT2RP3001495". Thus, it can be stated that "C-NT2RP3001495" is a novel protein found for the first time by the present inventors. The protein "C-NT2RP3001495" is a protein consisting of 414 amino acids which contains two WW domain sequences, and is associated with the maintenance of differentiation of smooth muscle cells.

Furthermore, after the identification of the novel protein "C-NT2RP3001495" by the present inventors, a result of homology search by BLASTN revealed that the sequence was identical to that deposited under an accession number AF211943 (submitted on Dec. 7, 1999; published on May 5, 2000) in GenBank by Bednarek A K et al. (University of Texas MD Anderson Cancer Center). (WWOX, a novel WW domain-containing protein mapping to human chromosome 16q23.3-24.1, a region frequently affected in breast cancer, Cancer Res. 60(8): 2140-2145, 2000).

EXAMPLE 6

Expression Analysis of Chicken "12F08"

The expression level of the gene, chicken "12F08", was analyzed by real-time PCR using ABI PRISM(R) 7700 Sequence Detection System from PE Biosystems (PCR Meth. And Appl. 4:357-362, 1995). By using oligonucleotides of sequence 8 (5'-GGT GGC TTT GCT GGA T1A TCT T-3'/SEQ ID NO:11) and sequence 9 (5'-GTT GCA GGA GGT CTG CCA TAT G-3'/SEQ ID NO:12), as well as G3PDH as an indicator, the expression levels of the mRNA were compared with one another among chicken aorta (Ao), AoSMC cell derived from the aorta (AoDD), A (differentiated primary culture cell of chicken gizzard smooth muscle), B (dedifferentiated primary culture cell of chicken gizzard smooth muscle by the addition of anti-IGF-I antibody), C (differentiated primary culture cell of chicken gizzard smooth muscle by the addition of control antibody), F1 (dedifferentiated primary culture cell of chicken gizzard smooth muscle one day after the addition of FCS), Br (brain), Ca (cardiac muscle), Gz (gizzard), and Lv (liver). The total RNAs, which had been extracted from chicken tissues of aorta (Ao), Br, Ca, Gz, and Lv directly obtained from a chicken, were kindly provided by Dr. Sobue at Osaka University. CAOMC (TC354-05) from Cell Applications, Inc. had been purchased from Toyobo. These cells were cultured according to the instructions in the protocol, and were used as AoSMC (AoDD) cells.

The results of real-time RT-PCR with AB17700 are shown in Table 1. PCR was carried out with pre-heating at 95° C. for 10 minutes, and 50 cycles of denaturation at 94° C. for 20 seconds, annealing at 55° C. for 20 seconds, and extension at 72° C. for 30 seconds by using SYBR Green PCR Core Reagent kit (PE Biosystems; 4304886). Each value is obtained by dividing the value of 12F08 expression level by the value of expression level of G3PDH as a control. The greater the value is, the higher the expression level of 12F08 gene in the cells will be. The chicken "12F08" was found to be expressed at a high level in differentiated smooth muscle and gizzard. Accordingly, it was suggested that the chicken "12F08" gene encodes a protein participating in the maintenance of differentiation of smooth muscle cells.

TABLE 1

| Tissue Cells | mRNA expression amount |
|---|---|
| Ao | 17.14 |
| AoDD | 0.88 |
| A | 3.43 |
| B | 2.37 |
| C | 8.4 |
| F1 | 2.18 |
| Br | 4.45 |
| Ca | 2.36 |
| Gz | 6.41 |
| Lv | 1.35 |

EXAMPLE 7

Gene Expression Analysis by Hybridization Using High Density DNA Filter

DNA for spotting onto the nylon membranes was prepared according to the following procedure. E. coli was cultured in each well of a 96-well plate (in a LB medium at 37° C. for 16 hours). A part of each culture was suspended in 10 µl of sterile water in the well of a 96-well plate. The plate was heated at 100° C. for 10 minutes. Then the samples were analyzed by PCR. PCR was performed in a 20 µl solution per one reaction by using TaKaRa PCR Amplification Kit (Takara) according to the supplier's protocol. A pair of sequencing primers, ME761FW (5' tacggaagtgttacttctgc 3'/SEQ ID NO:13) and ME1250RV (5' tgtgggaggtttttctcta 3'/SEQ ID NO:14), or a pair of primers, M13M4 (5' gttttcccagtcacgac 3'/SEQ ID NO:15) and M13RV (5' caggaaacagctatgac 3'/SEQ ID NO:16) were used for the amplification of the insert cDNA in the plasmid. PCR was performed in a thermal cycler, Gene-Amp System 9600 (PE Biosystems). The cycling profile consisted of pre-heating at 95° C. for 5 minutes; 10 cycles of denaturation at 95° C. for 10 seconds, and annealing/extension at 68° C. for 1 minute; 20 cycles of denaturation at 98° C. for 20 seconds and annealing/extension at 60° C. for 3 minutes; and final extension at 72° C. for 10 minutes. After the PCR, 2 µl of the reaction solution was electrophoresed on a 1% agarose gel. DNA on the gel was stained with ethidium bromide to confirm the amplification of cDNA. When cDNAs were not amplified by PCR, plasmids containing the corresponding insert cDNAs were prepared by the alkali-extraction method (Sambrook et al., Molecular Cloning, A laboratory manual/2nd edition, Cold Spring Harbor Laboratory Press, 1989).

DNA array was prepared by the following procedure. An Aliquot of the DNA solution was added to each well of a 384-well plate. DNA was spotted onto a nylon membrane (Boehringer) by using a 384-pin tool of Biomek 2000 Laboratory Automation System (Beckman-Coulter). More specifically, the 384-well plate containing the DNA was placed under the 384-pin tool. The independent 384 needles of the pin tool were simultaneously dipped into the DNA solution to fix the DNA on the needles. The needles were gently pressed onto a nylon membrane, and the DNA fixed on the needles was spotted onto the membrane. Denaturation of the spotted DNA and immobilization of the DNA on the nylon membrane were carried out according to conventional methods (Sambrook et al., Molecular Cloning, A laboratory manual/2nd edition, Cold Spring Harbor Laboratory Press, 1989).

1st strand cDNA labeled with radioisotope was used as the hybridization probe. The 1st strand cDNA was synthesized by using Thermoscript™ RT-PCR System (GIBCO). More specifically, the 1st strand cDNA was synthesized by using 1.5 μg mRNAs from various human tissues (Clontech), 1 μl 50 μM Oligo(dT)20, and 50 μCi [α$^{33}$P]dATP according to the attached protocol. Purification of the probe was carried out by using ProbeQuant™ G-50 micro column (Amersham-Pharmacia Biotech) according to the attached protocol. In the next step, 2 units of *E. coli* RNaseH were added to the reaction mixture. The mixture was incubated at room temperature for 10 minutes, and then 100 μg of human COT-1 DNA (GIBCO) was added thereto. The mixture was incubated at 97° C. for 10 minutes, and then was allowed to stand on ice to give the hybridization probe.

Hybridization of the radioisotope-labeled probe to the DNA array was performed in a usual manner (Sambrook et al., Molecular Cloning, A laboratory manual/2nd edition, Cold Spring Harbor Laboratory Press, 1989). The membrane was washed as follows: the nylon membrane was washed three times by incubating in the Washing solution 1 (2×SSC, 1% SDS) at room temperature (about 26° C.) for 20 minutes; then the membrane was washed 3 times by incubating it in the Washing solution 2 (0.1×SSC, 1% SDS) at 65° C. for 20 minutes. Autoradiography was performed by using an image plate for BAS2000 (Fuji Photo Film Co., Ltd.). Specifically, the nylon membrane used for the hybridization was wrapped with a piece of Saran Wrap, and was contacted with the light-sensitive surface of the image plate. The membrane with the image plate was placed in an imaging cassette for radioisotope and was allowed to stand in dark for 4 hours. The radioactivity recorded on the image plate was analyzed by BAS2000 (Fuji Photo Film Co., Ltd.) and was recorded as an image file of the autoradiogram by electronic conversion. The signal intensity of each DNA spot was analyzed by using Visage High Density Grid Analysis Systems (Genomic Solutions Inc.). The signal intensity was converted into numerical data. The data were taken by duplicated measurements. The reproducibility was assessed by comparing the signal intensities of the corresponding spots on the duplicated DNA filters that were hybridized to a single DNA probe. The ratio between the corresponding spots falls within a range of 2-folds or less in 95% of entire spots, and the correlation coefficient was r=0.97. Thus, the reproducibility was assumed to be satisfactory.

The detection sensitivity in gene expression analysis was estimated by examining increases in the signal intensity of the probe concentration-dependent spot of the hybridization using a probe complementary to the DNA spotted on the nylon membrane. PLACE1008092 (the same DNA as that deposited in GenBank Accession No. AF107253) was used as the DNA. The DNA array with the DNA of PLACE1008092 was prepared according to the above-mentioned method. The probe was prepared as follows: mRNA was synthesized in vitro from the clone, PLACE1008092; using this mRNA as the template, radioisotope-labeled 1st strand cDNA was synthesized in the same manner as the probe preparation method described above; and the cDNA was used as the probe. The cDNA PLACE1008092 was inserted into pBluescript SK(−), so that the 5'-end of the PLACE1008092 is ligated to the T7 promoter of the pBluescript SK(−) to give a recombinant plasmid for in vitro synthesis of the mRNA from PLACE1008092. Specifically, the PLACE1008092 inserted at the DraIII site of the pME18SFL3 was cut out by XhoI digestion. The resulting PLACE1008092 fragment was ligated to XhoI-predigested pBluescript SK(−) by using the DNA ligation kit ver.2 (Takara). The in-vitro mRNA synthesis from PLACE1008092 inserted in pBluescript SK(−) was carried out by using the Ampliscribe™ T7 high yield transcription kit (Epicentre technologies). The hybridization and analysis of signal intensity of each DNA spot were conducted using the same methods described above. When the probe concentration was 1×10$^7$ μg/ml or less, there was no increase of signal intensity proportional to the probe concentration. Therefore it was assumed to be difficult to compare the signals with one another in this concentration range. Thus, spots with a intensity of 40 or less were indiscriminately taken as low-level signals (FIG. 3). Within a concentration of the probe ranging from 1×10$^7$ μg/ml to 0.1 μg/ml, signals were found to increase in a probe concentration-dependent manner. The detection sensitivity is 1:100,000 in a ratio of mRNA expression level in a sample.

Table 2 shows the expression of each cDNA in human normal tissues (heart, lung, pituitary gland, thymus, brain, kidney, liver and spleen). The expression levels are indicated by numerical values of 0 to 10,000. The "C-NT2RP3001495" was expressed in at least one tissue.

TABLE 2

| Clone name | Heart | Lung | Pituitary gland | Thymus | Brain | Kidney | Liver | Spleen |
|---|---|---|---|---|---|---|---|---|
| GAPDH | 38.210 | 32.670 | 23.820 | 13.580 | 11.230 | 21.120 | 24.910 | 22.440 |
| β-actin | 279.280 | 368.870 | 111.100 | 117.500 | 92.880 | 114.650 | 82.990 | 256.790 |
| NT2RP3 001495 | 42.340 | 19.294 | 36.741 | 7.565 | 17.241 | 28.985 | 27.157 | 19.314 |

EXAMPLE 8

Analysis of Genes Associated with Neural Cell Differentiation

Genes involved in neural cell differentiation are useful for treating neurological diseases. It is possible that genes with varying expression levels in response to induction of cellular differentiation in neural cells are associated with neurological diseases. It was examined whether the expression of "C-NT2RP3001495" varies in response to induction of differentiation (stimulation by retinoic acid (RA)) in cultured cells of a neural strain, NT2.

The NT2 cells were treated basically according to the supplier's instruction manual. The term "undifferentiated NT2 cells" refers to NT2 cells successively cultured in an OPTI-MEM I (GIBCO BRL; catalog No. 31985) containing 10% (v/v) fetal bovine serum (GIBCO BRL) and 1% (v/v) penicillin-streptomycin (GIBCO BRL). The term "NT2 cells cultured in the.presence of retinoic acid" refers to cells passaged for 5 weeks following transferring of the undifferentiated NT2 cells into a retinoic acid-containing medium, which consists of D-MEM (GIBCO BRL; catalog No. 11965), 10% (v/v) fetal bovine serum, 1% (v/v) penicillin-streptomycin and 10 μM retinoic acid (GIBCO BRL). The term "NT2 cells that were cultured in the presence of retinoic acid, and which were further cultured in a media with the addition of cell-division inhibitor" refers to NT2 cells passaged for 2 weeks following transferring of the NT2 cells cultured in the presence of retinoic acid for 5 weeks into a cell-division inhibitor-containing medium, which consisted of D-MEM (GIBCO BRL; catalog No. 11965), 10% (v/v) fetal bovine serum, 1% (v/v) penicillin-streptomycin, 10 μM retinoic acid, 10 μM FudR (5-fuoro-2'-deoxyuridine: GIBCO BRL), 10 μM Urd (Uridine: GIBCO BRL) and 1 μM araC (Cytosine β-D-Arabinofuranoside: GIBCO BRL). Each of the cells were treated with trypsin and then were harvested. Total RNAs were extracted from the cells by using S.N.A.P.™ Total RNA Isolation kit (Invitrogen). The probe used for hybridization was labeled by using 10 μg of the total RNA according to the same methods as described above.

The data were obtained in triplicate (n=3). The data of signal value representing gene expression level in the cells in the presence of stimulation for inducing differentiation were compared with those without the stimulation. The comparison was performed by statistical treatment of two-sample t-test. Clones with significant difference in the signal distribution were selected under the condition of $p<0.05$. In this analysis, clones with difference can be statistically detected even when the signals are low. Accordingly, clones with signal value of 40 or less were also assessed.

Table 3 shows the expression level of "C-NT2RP3001495" cDNA in undifferentiated NT2 cells, NT2 cells cultured in the presence of RA, and NT2 cells cultured with the addition of cell-division inhibitor after culturing in the presence of RA.

Averaged signal values ($M_1$, $M_2$) and sample variances ($s_1^2$, $s_2^2$) were calculated for each gene in each of the cells, and then, the pooled sample variances $s^2$ were obtained from the sample variances of the two types of cells to be compared. The t values were determined according to the following formula: $t=(M_1-M_2)/s/(\frac{1}{3}+\frac{1}{3})^{1/2}$. When the determined t-value was greater than a t-value at P, the probability of significance level, of 0.05 or 0.01 in the t-distribution table with 4 degrees of freedom, it was judged there exists a difference in the expression level of the genes between the two types of cells at $P<0.05$ or $P<0.01$, respectively. The table also includes the information on an increase (+) or decrease (-) in the average expression level of a signal in the clones compared with that of undifferentiated cells.

As a result, the expression of the "C-NT2RP3001495" was shown to increase by RA, suggesting that it is a clone involved in neurological disorders.

EXAMPLE 9

Analysis of Rheumatoid Arthritis-associated Genes

Proliferation of synovial cells covering inner surfaces of joint cavity and inflammatory reaction resulted from the action of cytokines produced by leukocytes infiltrating into the joint synovial tissues is thought to be involved in the onset of rheumatoid arthritis (Japan Rheumatism Foundation Information Center). Recent studies have also revealed that tissue necrosis factor (TNF)=χ participates in the onset of rheumatoid arthritis (Current opinion in immunology 1999, 11, 657-662). Those genes whose expression level changes in response to the action of TNF on synovial cells are considered to be involved in rheumatoid arthritis. It was examined whether the expression of "C-NT2RP3001495" varies in response to TNF=χ in the primary cell culture of synovial tissue.

The primary cultured synovial cells (Cell Applications) were grown to be confluent in a culture dish, and then, human TNF-α (Boehringer-Mannheim) was added at a final concentration of 10 ng/ml thereto. The culture was further continued for 24 hours. Total RNA was extracted from the cells by using S.N.A.P.™ Total RNA Isolation kit (Invitrogen). The labeling of the probe used for hybridization was carried out by using 10 μg of the total RNA according to the same methods as described above. The data were obtained in triplicate (n=3). The data of signal value representing gene expression level in cells with TNF stimulation were compared with those without the stimulation. The comparison was performed by statistical treatment of two-sample t-test. Clones with significant difference in the signal distribution were selected under the condition of $p<0.05$. According to the analysis, clones with difference can be statistically detected even when the signals were low. Accordingly, clones with signal value of 40 or less were also assessed for the selection.

Table 4 shows the expression level of each cDNA in synovial cells cultured under the absence or presence of TNF. Averaged signal values ($M_1$, $M_2$) and sample variances ($s_1^2$, $s_2^2$) for each gene were calculated in each of the cells, and then, the pooled sample variances $s^2$ were obtained from the sample variances of the two types of cells to be compared. The t-values were determined according to the following formula: $t=(M_1-M_2)/s/(\frac{1}{3}+\frac{1}{3})^{1/2}$. When the determined t-value was greater than a t-value at P, probability of significance level, of 0.05 or 0.01 in the t-distribution table with 4 degrees of freedom, it was judged that a difference exists in the expression level of the gene between the two types of cells at $P<0.05$ or $P<0.01$, respectively. The table also includes the

TABLE 3

| Clone | NT2 | | | NT2 RA | | | NT2 RA INHIB | | | ttest | + | ttest | + |
|---|---|---|---|---|---|---|---|---|---|---|---|---|---|
| | exp. 1 | exp. 2 | exp. 3 | exp. 1 | exp. 2 | exp. 3 | exp. 1 | exp. 2 | exp. 3 | N/R | – | N/I | – |
| GAPDH(Cr1) | 3.53 | 1.08 | 0.98 | 2.92 | 2.49 | 2.8 | 1.76 | 2.59 | 1.52 | | | | |
| β actin(Cr2) | 155.38 | 118 | 99.68 | 148.45 | 110.68 | 101.34 | 114.68 | 105.79 | 151.13 | | | | |
| NT2RP3001495 | 4.27 | 2.41 | 2.48 | 4.72 | 5.59 | 4.95 | 3.72 | 4.06 | 3.66 | * | + | | | information of an increase (+) or decrease (−) in the average expression level of a signal in the clones compared with that of undifferentiated cells.

The results showed that the expression level of "C-NT2RP3001495" was reduced by TNF-α, suggesting that it is a clone associated with Rheumatoid arthritis.

TABLE 4

| Clone | Synoviocyte | | | Synoviocute_TNF | | | t test vs TNF | + − |
|---|---|---|---|---|---|---|---|---|
| | exp. 1 | exp. 2 | exp. 3 | exp. 1 | exp. 2 | exp. 3 | | |
| GAPDH(Cr1) | 0.4 | 0.8 | 0.89 | 0.9 | 1 | 1.15 | | |
| β actin(Cr2) | 385.94 | 262.23 | 582.98 | 443.28 | 422.61 | 573.47 | | |
| NT2RP3001495 | 4.14 | 4.14 | 3.85 | 2.75 | 2.92 | 1.76 | * | − |

EXAMPLE 10

Analysis of Ultraviolet Radiation Damage-associated Genes

It is known that ultraviolet rays give considerably adverse influence on health. In recent years, the risks of tissue damage by ultraviolet rays has been increased due to the destruction of the ozone layer, and ultraviolet radiation has been recognized as a risk factor for diseases such as skin cancers (United States Environmental Protection Agency: Ozone Depletion Home Page, http://www.epa.gov/ozone/). Genes whose expression levels change with exposure of the skin epidermal cells to ultraviolet rays are considered to be associated with skin damage caused by ultraviolet radiation. Culturing primary cultured skin fibroblast cells irradiated with ultraviolet ray, it was examined whether the expression of "C-NT2RP3001495" varies depending on the irradiation of ultraviolet ray.

First, after culturing to confluence in a culture dish, the primary cultured skin fibroblast cells (Cell Applications) were exposed to 10,000 μj/cm$^2$ of 254-nm ultraviolet light. Thereafter, messenger RNAs were extracted by using a Fast-Track™ 2.0 mRNA Isolation kit (Invitrogen) from the unexposed cells and from the cells that were exposed to the ultraviolet light and then cultured for 4 or 24 hours. The labeling of the hybridization probe was carried out by using 1.5 μg of each mRNA in the same manner as described above. The data were obtained in triplicate (n=3). The hybridization signals were compared between the cells exposed to the ultraviolet light and the unexposed cells. The comparison was preformed by statistical treatment with two-sample t-test. Clones with significant differences in the signal distribution were selected under the condition of p<0.05. According to the analysis, the difference in the signal values can be also detected statistically even when the signal values are low. Accordingly, clones with signal value of 40 or lower were also assessed.

Table 5 shows the expression of each cDNA in skin-derived fibroblast cells exposed and unexposed to ultraviolet light.

Averaged signal values ($M_1$, $M_2$) and sample variances ($s_1^2$, $s_2^2$) were calculated for each gene in each of the cells, and then, pooled sample variances $s^2$ were obtained from the sample variances of the two types of cells to be compared. The t values were determined according to the following formula: $t=(M_1-M_2)/s/(⅓+⅓)^{1/2}$. When the determined t-value was greater than a t-value at P, probability of significance level, of 0.05 or 0.01 in the t-distribution table with 4 degrees of freedom, it was judged that a difference exists in the expression level of the gene between the two types of cells at P<0.05 or P<0.01, respectively. The table also includes the information of an increase (+) or decrease (−) in the average expression level of a signal in the clones compared with that of undifferentiated cells.

The results showed that the expression level of "C-NT2RP3001495" was reduced 4 hours or 24 hours after ultraviolet ray irradiation, suggesting that it is a clone associated with ultraviolet ray disorders.

TABLE 5

| Clone | UV_0 h | | | UV_4 h | | | UV_24 h | | | t test | | 4 h | 24 h |
|---|---|---|---|---|---|---|---|---|---|---|---|---|---|
| | Exp. 1 | Exp. 2 | Exp. 3 | Exp. 1 | Exp. 2 | Exp. 3 | Exp. 1 | Exp. 2 | Exp. 3 | 0/4 | 0/24 | +/− | +/− |
| GAPDH(Cr1) | 0 | 1.29 | 0.1 | 0.9 | 0.06 | 1.18 | 1.49 | 0.47 | 0 | | | | |
| β actin(Cr2) | 256.82 | 283.53 | 414.29 | 388.38 | 117.29 | 329.8 | 189.18 | 190.26 | 151.87 | | * | | − |
| NT2RP3001495 | 18.56 | 21.11 | 19.03 | 12.08 | 9.76 | 9.93 | 15.89 | 18.33 | 21.35 | ** | | − | |

INDUSTRIAL APPLICABILITY

The present invention provides a novel human protein "C-NT2RP3001495" associated with the maintenance of differentiation of smooth muscle cells and the gene encoding the protein. The protein has two WW domains that participate in protein-protein interaction. Thus, it is presumed that the protein regulates intracellular signal transduction, gene expression and others through binding with other proteins, and thereby participates in the maintenance of differentiation of smooth muscle cells. Abnormalities in the maintenance of differentiation of smooth muscle cells have been known to cause a variety of diseases. For example, phenotypic modulation of vascular tunica media smooth muscle cell to a dedifferentiated type is recognized in the early phases of the onset of arteriosclerosis and is known as the major cause of thickening of vascular endothelium. Thus, the protein of the present invention participating in the maintenance of differentiation of smooth muscle cells is considered to play important roles in living body, and accordingly, it is useful as a target molecule in drug development. Further, compounds controlling functions of the inventive protein are expected to be pharmaceuticals for a variety of diseases caused by the abnormality in the maintenance of differentiation of smooth muscle cells, for example, ischemic heart diseases such as arteriosclerosis, myocardial infarction, aortic aneurysm, and cerebral apoplexy; cerebral vascular disorders; vascular dementia; as well as glomerulonephritis, pulmonary fibrosis, cerebral arteriosclerosis, hepatitis, and such, that are states of aberrant proliferation of mesangial cells, alveolar epithelial cells, pericytes, and Ito cells, cells which have extremely similar characteristics to those of the smooth muscle cell.

What is claimed is:

1. An antibody that binds to a purified polypeptide consisting of the amino acid sequence of SEQ ID NO:2.

2. A method for generating an antibody, the method comprising immunizing an animal with a purified polypeptide consisting of the amino acid sequence of SEQ ID NO:2.

* * * * *

SEQUENCE LISTING

```
<160> NUMBER OF SEQ ID NOS: 16

<210> SEQ ID NO 1
<211> LENGTH: 2256
<212> TYPE: DNA
<213> ORGANISM: Homo sapiens
<220> FEATURE:
<221> NAME/KEY: CDS
<222> LOCATION: (125)..(1366)

<400> SEQUENCE: 1
cagtgcgcag gcgtgagcgg tcgggccccg acgcgcgcgg gtctcgtttg gagcgggagt      60
gagttcctga gcgagtggac ccggcagcgg gcgatagggg ggccaggtgc ctccacagtc     120 agcc atg gca gcg ctg cgc tac gcg ggg ctg gac gac acg gac agt gag     169
     Met Ala Ala Leu Arg Tyr Ala Gly Leu Asp Asp Thr Asp Ser Glu
      1               5                  10                  15 gac gag ctg cct ccg ggc tgg gag gag aga acc acc aag gac ggc tgg     217
Asp Glu Leu Pro Pro Gly Trp Glu Glu Arg Thr Thr Lys Asp Gly Trp
                20                  25                  30 gtt tac tac gcc aat cac acc gag gag aag act cag tgg gaa cat cca     265
Val Tyr Tyr Ala Asn His Thr Glu Glu Lys Thr Gln Trp Glu His Pro
            35                  40                  45 aaa act gga aaa aga aaa cga gtg gca gga gat ttg cca tac gga tgg     313
Lys Thr Gly Lys Arg Lys Arg Val Ala Gly Asp Leu Pro Tyr Gly Trp
        50                  55                  60 gaa caa gaa act gat gag aac gga caa gtg ttt ttt gtt gac cat ata     361
Glu Gln Glu Thr Asp Glu Asn Gly Gln Val Phe Phe Val Asp His Ile
    65                  70                  75 aat aaa aga acc acc tac ttg gac cca aga ctg gcg ttt act gtg gat     409
Asn Lys Arg Thr Thr Tyr Leu Asp Pro Arg Leu Ala Phe Thr Val Asp
 80                  85                  90                  95 gat aat ccg acc aag cca acc acc cgg caa aga tac gac ggc agc acc     457
Asp Asn Pro Thr Lys Pro Thr Thr Arg Gln Arg Tyr Asp Gly Ser Thr
               100                 105                 110 act gcc atg gaa att ctc cag ggc ccg gat ttc act ggc aaa gtg gtt     505
Thr Ala Met Glu Ile Leu Gln Gly Pro Asp Phe Thr Gly Lys Val Val
           115                 120                 125 gtg gtc act gga gct aat tca gga ata ggg ttc gaa acc gcc aag tct     553
Val Val Thr Gly Ala Asn Ser Gly Ile Gly Phe Glu Thr Ala Lys Ser
       130                 135                 140 ttt gcc ctc cat ggt gca cat gtg atc ttg gcc tgc agg aac atg gca     601
Phe Ala Leu His Gly Ala His Val Ile Leu Ala Cys Arg Asn Met Ala
   145                 150                 155 agg gcg agt gaa gca gtg tca cgc att tta gaa gaa tgg cat aaa gcc     649
Arg Ala Ser Glu Ala Val Ser Arg Ile Leu Glu Glu Trp His Lys Ala
160                 165                 170                 175 aag gta gaa gca atg acc ctg gac ctc gct ctc ctc cgt agc gtg cag     697
Lys Val Glu Ala Met Thr Leu Asp Leu Ala Leu Leu Arg Ser Val Gln
               180                 185                 190 cat ttt gct gaa gca ttc aag gcc aag aat gtg cct ctt cat gtg ctt     745
His Phe Ala Glu Ala Phe Lys Ala Lys Asn Val Pro Leu His Val Leu
           195                 200                 205 gtg tgc aac gca gca act ttt gct cta ccc tgg agt ctc acc aaa gat     793
```

```
                Val Cys Asn Ala Ala Thr Phe Ala Leu Pro Trp Ser Leu Thr Lys Asp
                    210                 215                 220 ggc ctg gag acc acc ttt caa gtg aat cat ctg ggg cac ttc tac ctt         841
Gly Leu Glu Thr Thr Phe Gln Val Asn His Leu Gly His Phe Tyr Leu
        225                 230                 235 gtc cag ctc ctc cag gat gtt ttg tgc cgc tca gct cct gcc cgt gtc         889
Val Gln Leu Leu Gln Asp Val Leu Cys Arg Ser Ala Pro Ala Arg Val
240                 245                 250                 255 att gtg gtc tcc tca gag tcc cat cga ttt aca gat att aac gac tcc         937
Ile Val Val Ser Ser Glu Ser His Arg Phe Thr Asp Ile Asn Asp Ser
                260                 265                 270 ttg gga aaa ctg gac ttc agt cgc ctc tct cca aca aaa aac gac tat         985
Leu Gly Lys Leu Asp Phe Ser Arg Leu Ser Pro Thr Lys Asn Asp Tyr
            275                 280                 285 tgg gcg atg ctg gct tat aac agg tcc aag ctc tgc aac atc ctc ttc        1033
Trp Ala Met Leu Ala Tyr Asn Arg Ser Lys Leu Cys Asn Ile Leu Phe
        290                 295                 300 tcc aac gag ctg cac cgt cgc ctc tcc cca cgc ggg gtc acg tcg aac        1081
Ser Asn Glu Leu His Arg Arg Leu Ser Pro Arg Gly Val Thr Ser Asn
305                 310                 315 gca gtg cat cct gga aat atg atg tac tcc aac att cat cgc agc tgg        1129
Ala Val His Pro Gly Asn Met Met Tyr Ser Asn Ile His Arg Ser Trp
320                 325                 330                 335 tgg gtg tac aca ctg ctg ttt acc ttg gcg agg cct ttc acc aag tcc        1177
Trp Val Tyr Thr Leu Leu Phe Thr Leu Ala Arg Pro Phe Thr Lys Ser
                340                 345                 350 atg caa cag gga gct gcc acc acc gtg tac tgt gct gct gtc cca gaa        1225
Met Gln Gln Gly Ala Ala Thr Thr Val Tyr Cys Ala Ala Val Pro Glu
            355                 360                 365 ctg gag ggt ctg gga ggg atg tac ttc aac aac tgc tgc cgc tgc atg        1273
Leu Glu Gly Leu Gly Gly Met Tyr Phe Asn Asn Cys Cys Arg Cys Met
        370                 375                 380 ccc tca cca gaa gct cag agc gaa gag acg gcc cgg acc ctg tgg gcg        1321
Pro Ser Pro Glu Ala Gln Ser Glu Glu Thr Ala Arg Thr Leu Trp Ala
    385                 390                 395 ctc agc gag agg ctg atc caa gaa cgg ctt ggc agc cag tcc ggc            1366
Leu Ser Glu Arg Leu Ile Gln Glu Arg Leu Gly Ser Gln Ser Gly
400                 405                 410 taagtggagc tcagagcgga tgggcacaca cacccgccct gtgtgtgtcc cctcacgcaa      1426
gtgccagggc tgggccccct tccaaatgtcc ctccaacaca gatccgcaag agtaaaggaa    1486
ataagagcag tcacaacaga gtgaaaaatc ttaagtacca atgggaagca gggaattcct     1546
ggggtaaagt atcactttc tggggctggg ctaggcatag gtctctttgc tttctggtgg      1606
tggcctgttt gaaagtaaaa acctgcttgg tgtgtaggtt ccgtatctcc ctggagaagc     1666
accagcaatt ctctttcttt tactgttata gaatagcctg aggtcccctc gtcccatcca     1726
gctaccacca cggccaccac tgcagccggg ggctggcctt ctcctactta gggaagaaaa     1786
agcaagtgtt cactgctcct tgctgcattg atccaggaga taattgtttc attcatcctg    1846
accaagactg agccagctta gcaactgctg gggagacaaa tctcagaacc ttgtcccagc    1906
cagtgaggat gacagtgaca cccagaggga gtagaatacg cagaactacc aggtggcaaa    1966
gtacttgtca tagactcctt tgctaatgct atgcaaaaaa ttctttagag attataacaa    2026 attttcaaa tcattcctta gataccttga aaggcaggaa gggaagcgta tacttaag      2086 aatacacagg atattttggg gggcagagaa taaaacgtta gttaatccct ttgtctgtca    2146
atcacagtct cagttctctt gctttcacat tgtacttaaa cctcctgctg tgcctcgcat    2206
cctatgctta ataaaagaac atgcttgaat atcaaaaaaa aaaaaaaaac              2256
```

-continued

<210> SEQ ID NO 2
<211> LENGTH: 414
<212> TYPE: PRT
<213> ORGANISM: Homo sapiens

<400> SEQUENCE: 2

Met Ala Ala Leu Arg Tyr Ala Gly Leu Asp Asp Thr Asp Ser Glu Asp
1               5                   10                  15

Glu Leu Pro Pro Gly Trp Glu Arg Thr Thr Lys Asp Gly Trp Val
            20                  25                  30

Tyr Tyr Ala Asn His Thr Glu Lys Thr Gln Trp Glu His Pro Lys
        35                  40                  45

Thr Gly Lys Arg Lys Arg Val Ala Gly Asp Leu Pro Tyr Gly Trp Glu
    50                  55                  60

Gln Glu Thr Asp Glu Asn Gly Gln Val Phe Phe Val Asp His Ile Asn
65                  70                  75                  80

Lys Arg Thr Thr Tyr Leu Asp Pro Arg Leu Ala Phe Thr Val Asp Asp
                85                  90                  95

Asn Pro Thr Lys Pro Thr Thr Arg Gln Arg Tyr Asp Gly Ser Thr Thr
            100                 105                 110

Ala Met Glu Ile Leu Gln Gly Pro Asp Phe Thr Gly Lys Val Val Val
        115                 120                 125

Val Thr Gly Ala Asn Ser Gly Ile Gly Phe Glu Thr Ala Lys Ser Phe
130                 135                 140

Ala Leu His Gly Ala His Val Ile Leu Ala Cys Arg Asn Met Ala Arg
145                 150                 155                 160

Ala Ser Glu Ala Val Ser Arg Ile Leu Glu Glu Trp His Lys Ala Lys
                165                 170                 175

Val Glu Ala Met Thr Leu Asp Leu Ala Leu Leu Arg Ser Val Gln His
            180                 185                 190

Phe Ala Glu Ala Phe Lys Ala Lys Asn Val Pro Leu His Val Leu Val
        195                 200                 205

Cys Asn Ala Ala Thr Phe Ala Leu Pro Trp Ser Leu Thr Lys Asp Gly
    210                 215                 220

Leu Glu Thr Thr Phe Gln Val Asn His Leu Gly His Phe Tyr Leu Val
225                 230                 235                 240

Gln Leu Leu Gln Asp Val Leu Cys Arg Ser Ala Pro Ala Arg Val Ile
                245                 250                 255

Val Val Ser Ser Glu Ser His Arg Phe Thr Asp Ile Asn Asp Ser Leu
            260                 265                 270

Gly Lys Leu Asp Phe Ser Arg Leu Ser Pro Thr Lys Asn Asp Tyr Trp
        275                 280                 285

Ala Met Leu Ala Tyr Asn Arg Ser Lys Leu Cys Asn Ile Leu Phe Ser
    290                 295                 300

Asn Glu Leu His Arg Arg Leu Ser Pro Arg Gly Val Thr Ser Asn Ala
305                 310                 315                 320

Val His Pro Gly Asn Met Met Tyr Ser Asn Ile His Arg Ser Trp Trp
                325                 330                 335

Val Tyr Thr Leu Leu Phe Thr Leu Ala Arg Pro Phe Thr Lys Ser Met
            340                 345                 350

Gln Gln Gly Ala Ala Thr Thr Val Tyr Cys Ala Ala Val Pro Glu Leu
        355                 360                 365

Glu Gly Leu Gly Gly Met Tyr Phe Asn Asn Cys Cys Arg Cys Met Pro
    370                 375                 380

```
Ser Pro Glu Ala Gln Ser Glu Glu Thr Ala Arg Thr Leu Trp Ala Leu
385                 390                 395                 400

Ser Glu Arg Leu Ile Gln Glu Arg Leu Gly Ser Gln Ser Gly
            405                 410

<210> SEQ ID NO 3
<211> LENGTH: 251
<212> TYPE: DNA
<213> ORGANISM: Gallus gallus
<220> FEATURE:
<221> NAME/KEY: CDS
<222> LOCATION: (3)..(251)

<400> SEQUENCE: 3 ag gag cgc acc acc aag gac ggc tgg gtt tac tac gcc aat cac ttg      47
   Glu Arg Thr Thr Lys Asp Gly Trp Val Tyr Tyr Ala Asn His Leu
   1               5                   10                  15 gaa gaa aaa aca cag tgg gaa cat cca aaa tct ggg aag agg aaa cgt     95
Glu Glu Lys Thr Gln Trp Glu His Pro Lys Ser Gly Lys Arg Lys Arg
            20                  25                  30 gtt gca gga ggt ctg cca tat gga tgg gag cag gag act gat gaa aat    143
Val Ala Gly Gly Leu Pro Tyr Gly Trp Glu Gln Glu Thr Asp Glu Asn
        35                  40                  45 gga cag gtc tat ttt gta gac cac ata aac aaa aga act acc tat ctg    191
Gly Gln Val Tyr Phe Val Asp His Ile Asn Lys Arg Thr Thr Tyr Leu
    50                  55                  60 gat cca aga ttg gcc ttt aca gtt gaa gat aat cca gca aag cca cct    239
Asp Pro Arg Leu Ala Phe Thr Val Glu Asp Asn Pro Ala Lys Pro Pro
65                  70                  75 act aga caa aaa                                                    251
Thr Arg Gln Lys
 80

<210> SEQ ID NO 4
<211> LENGTH: 83
<212> TYPE: PRT
<213> ORGANISM: Gallus gallus

<400> SEQUENCE: 4

Glu Arg Thr Thr Lys Asp Gly Trp Val Tyr Tyr Ala Asn His Leu Glu
1               5                   10                  15

Glu Lys Thr Gln Trp Glu His Pro Lys Ser Gly Lys Arg Lys Arg Val
            20                  25                  30

Ala Gly Gly Leu Pro Tyr Gly Trp Glu Gln Glu Thr Asp Glu Asn Gly
        35                  40                  45

Gln Val Tyr Phe Val Asp His Ile Asn Lys Arg Thr Thr Tyr Leu Asp
    50                  55                  60

Pro Arg Leu Ala Phe Thr Val Glu Asp Asn Pro Ala Lys Pro Pro Thr
65                  70                  75                  80

Arg Gln Lys

<210> SEQ ID NO 5
<211> LENGTH: 30
<212> TYPE: RNA
<213> ORGANISM: Artificial Sequence
<220> FEATURE:
<223> OTHER INFORMATION: Description of Artificial Sequence:
      Artificially Synthesized Sequence

<400> SEQUENCE: 5
agcaucgagu cggccuuguu ggccuacugg                                    30
```

```
<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 6
gcggctgaag acggcctatg tggcctttttt tttttttttt tt              42

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 7
agcatcgagt cggccttgtt g                                       21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 8
gcggctgaag acggcctatg t                                       21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 9
gcaggaacat ggcaagggcg agtg                                    24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 10
gggcaggagc tgagcggcac aaa                                     23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 11
ggtggctttg ctggattatc tt                                      22

<210> SEQ ID NO 12
```

-continued

```
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 12
gttgcaggag gtctgccata tg                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 13
tacggaagtg ttacttctgc                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 14
tgtgggaggt ttttctcta                                                  20

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 15
gttttcccag tcacgac                                                    17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 16
caggaaacag ctatgac                                                    17
```